(12) United States Patent
Jessen

(10) Patent No.: US 7,540,875 B2
(45) Date of Patent: Jun. 2, 2009

(54) SURGICAL CUTTING TOOL WITH AUTOMATICALLY RETRACTABLE BLADE ASSEMBLY

(75) Inventor: John W. Jessen, Seattle, WA (US)

(73) Assignee: AVATAR Design & Development, Inc., Seattle, WA (US)

( * ) Notice: Subject to any disclaimer, the term of this patent is extended or adjusted under 35 U.S.C. 154(b) by 0 days.

(21) Appl. No.: 10/457,040

(22) Filed: Sep. 22, 2003

(65) Prior Publication Data

US 2004/0039406 A1    Feb. 26, 2004

Related U.S. Application Data

(60) Continuation-in-part of application No. 10/160,571, filed on May 31, 2002, now abandoned, which is a division of application No. 09/324,091, filed on Jun. 1, 1999, now Pat. No. 6,402,770.

(60) Provisional application No. 60/087,783, filed on Jun. 1, 1998, provisional application No. 60/387,107, filed on Jun. 7, 2002.

(51) Int. Cl.
*A61B 17/32* (2006.01)
(52) U.S. Cl. .................................................. 606/167
(58) Field of Classification Search ................. 606/82, 606/167, 170, 171, 174, 185, 168, 172, 181, 606/182; 30/162, 272, 314, 335
See application file for complete search history.

(56) References Cited

U.S. PATENT DOCUMENTS

| | | | |
|---|---|---|---|
| 4,291,690 A | 9/1981 | Jessen | |
| 4,438,768 A | 3/1984 | Barrickman | |
| 4,578,865 A | 4/1986 | Keller | |
| 4,617,929 A | 10/1986 | Gill | |
| 4,715,121 A | 12/1987 | Sugiyama et al. | |
| 4,791,725 A | 12/1988 | Amagaya | |
| 4,877,021 A | 10/1989 | Higer et al. | |
| 5,147,316 A * | 9/1992 | Castillenti | 604/164.04 |
| 5,158,552 A * | 10/1992 | Borgia et al. | 604/164.12 |
| 5,215,526 A * | 6/1993 | Deniega et al. | 604/164.09 |
| 5,337,481 A | 8/1994 | Mears | |
| 5,522,831 A * | 6/1996 | Sleister et al. | 606/182 |
| 5,536,256 A * | 7/1996 | Yoon | 604/164.12 |
| 5,620,456 A * | 4/1997 | Sauer et al. | 606/185 |
| 5,853,392 A * | 12/1998 | Dennis | 604/164.01 |
| 6,086,606 A | 7/2000 | Knodel et al. | |

* cited by examiner

*Primary Examiner*—Eduardo C. Robert
*Assistant Examiner*—Michael J Araj
(74) *Attorney, Agent, or Firm*—Patrick M Dwyer

(57) ABSTRACT

Innovative disposable thoracostomy and cricothyrotomy trocar systems and new and improved methods for emergency management of upper airway obstructions and chest injuries are disclosed.

3 Claims, 18 Drawing Sheets

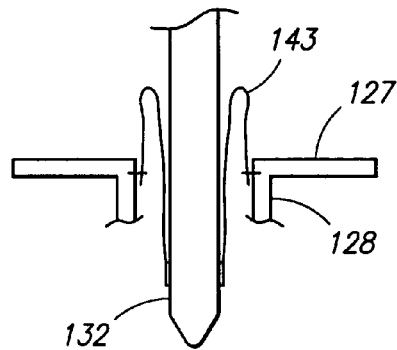
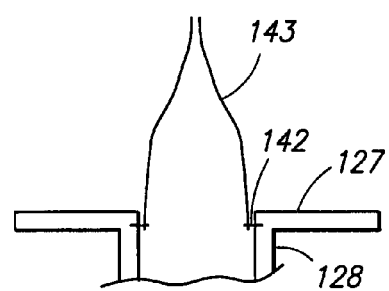
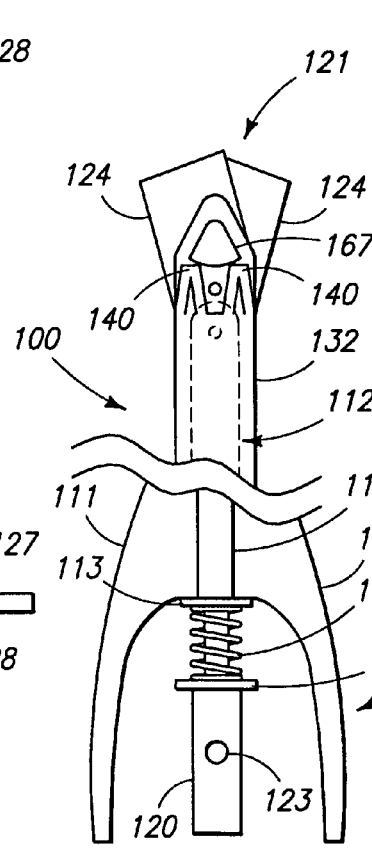
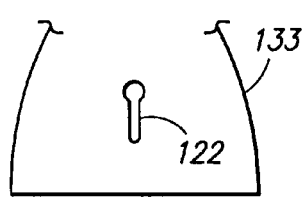
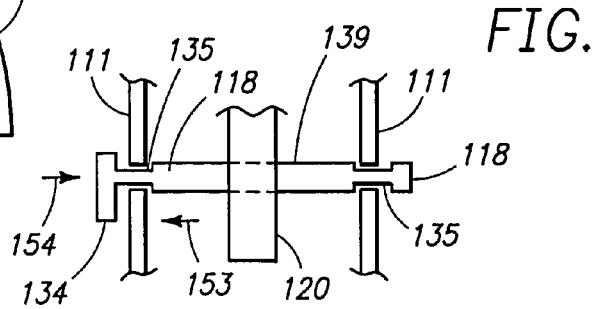
FIG. 11b
FIG. 9
FIG. 11a
FIG. 8a
FIG. 10
FIG. 8c
FIG. 8b

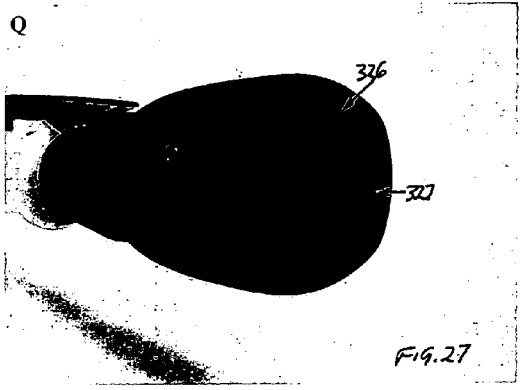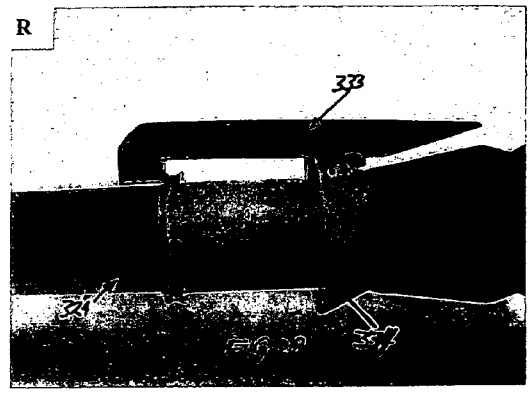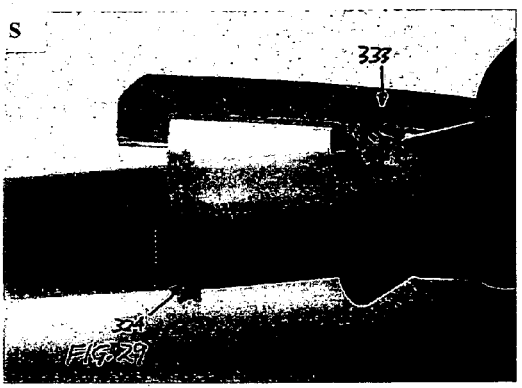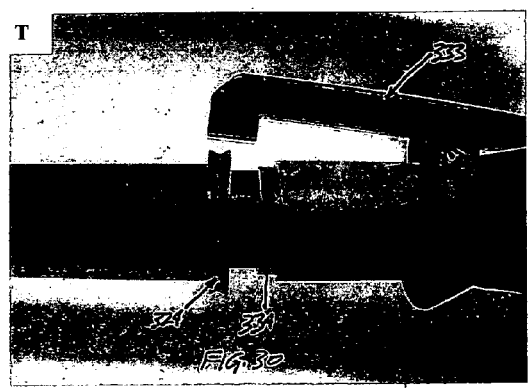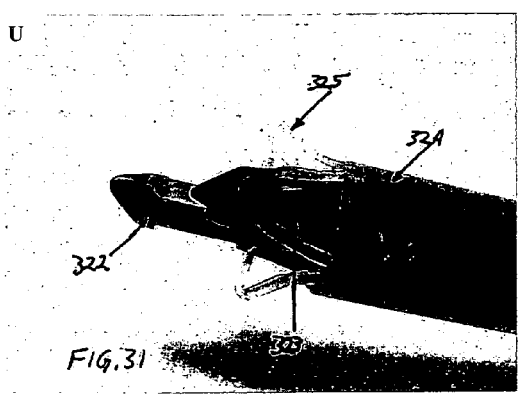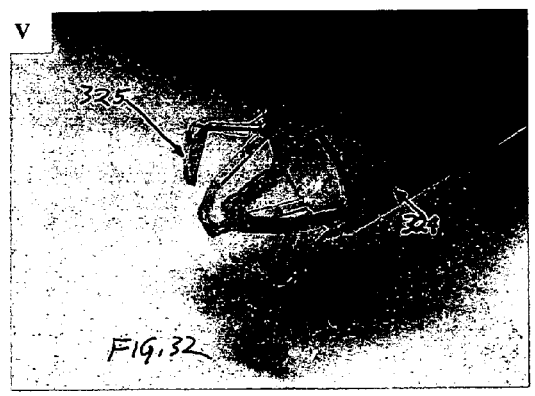

SURGICAL CUTTING TOOL WITH AUTOMATICALLY RETRACTABLE BLADE ASSEMBLY

This application is a continuation-in-part of U.S. patent application Ser. No. 10/160,571 filed May 31, 2002, now abandoned which is a division of Ser. No. 09/324,091 filed Jun. 1, 1999, now issued Jun. 11, 2002 as U.S. Pat. No. 6,402,770, which claimed priority to U.S. provisional application 60/087,783 filed Jun. 1, 1998; this application also claims priority to U.S. provisional application 60/387,107 filed Jun. 7, 2002.

TECHNICAL FIELD

The invention relates to emergency airway devices and emergency thoracostomy devices; more particularly, it relates to trocar devices and method and apparatus for a establishing and maintaining an emergency opening to a body cavity.

BACKGROUND OF THE INVENTION

A novel retractable trocar thoracostomy system is needed to replace the current needle thoracostomy technique that is used in emergency situations for patients who have tension pneumothorax, and to replace current chest tube insertion devices and procedures, as well as laparoscopic procedures. A retractable trocar should be quicker, easier and less traumatic than currently used techniques, provided, among other criteria, that the cutting mechanism used to enter the chest is designed not to injure deep structures.

DISCLOSURE OF THE INVENTION

Devices and methods disclosed herein solve the thoracostomy problems discussed above by, among other things, incorporating a twin-bladed, retractable incision mechanism, mounted within the end of a trocar. That is, not only is the trocar retractable, but the two part blades themselves are retractable within each trocar. Such devices make a precise incision greater than the width of the included cannula that is delivered with the trocar, and preferably about twice as wide as the I.D. of the cannula. The disclosed safe-ended cutting mechanism is retracted immediately upon entering the chest or abdomen, thus avoiding internal injury during full insertion of the blunted trocar shaft. The trocar shaft is then removed to leave a self-retaining plastic delivery cannula.

A surgical cutting tool is also disclosed. It has a "cam action" (the term defined further herein) retractable blade assembly with two blades, each with a blade edge and an angled blade point. Preferably, the blade assembly has two substantially identical blades each having an edge face with a single bevel cutting edge disposed at an angle to a longitudinal axis of the blade, each edge ending in a blade point at a distal end of the blade, each blade further having a pivot pin hole in a proximal region of the blade with a hole center lying on the blade axis. Also each blade has a cam slot distal to the pin hole with an distal cam slot center lying substantially on the blade axis and a proximal cam slot center lying substantially on a line between the pin hole center and the blade point. The two blades are pivotally mounted edge face to edge face upon the pivot pin engaged within both pin holes. The tool also has a cam pin, the cam pin relatively stationarily engaged (see below) within both cam slots, so that movement of the pivot pin in a distal direction urges the two blades to rotate their two blade points closer to each other in an extended configuration, and movement of the pivot pin in a proximal direction urges the two blades to rotate their two blade points further from each other in a closed or retracted configuration.

In the extended configuration, the two blades have overlapping blade points to form an extended blade profile, and the profile preferably has a relatively less sharp, "safe zone" (discussed further below) at its tip. The tool also has a spring and a pushrod engaging the blades to extend the blade assembly against spring resistance into a locked position when fully extended; the pushrod may advantageously be a wire, or other longitudinally flexible, but compression and stretch resistant, push-pull type linkage such as wire wound cable.

A improved cannula for surgical procedures is also provided. It is a self retaining cannula with a collapsible retention lattice at a distal end. In one aspect, the lattice is further comprised of struts, and the struts are formed in a partial frusto-conical (truncated cone shape) configuration at the distal end of the cannula. In another aspect, prior to assembly, the lattice structure is formed substantially flat, and the cannula is segmented, with cannula segments depending radially from the flat formed lattice. Alternatively, the cannula and lattice structure, after assembly, has four contiguous rectilinear zones defined by an intersecting pair of substantially perpendicular lines, a central portion of each of which is open or latticed.

A retractable trocar device is provided for placing and maintaining a percutaneous tube into a body cavity such as an airway, a chest cavity, or an abdominal cavity. The device has a cam action retractable blade assembly with two blades, each with its own blade edge and angled blade point. The blade assembly has two substantially identical blades each having an edge face with a single bevel cutting edge disposed at an angle to a longitudinal axis of the blade, each edge ending in a blade point at a distal end of the blade, the two blades pivotally mounted edge face to edge face upon a pivot pin, with the blade points overlapped in an extended configuration. The blade assembly of the trocar device desirably also has a "safe zone" at a tip of the extended configuration, as discussed above.

The trocar device has a handle enclosing at least a portion of a spring and a pushrod, with pushrod under spring tension or compression in an extended configuration, the pushrod engaging the blades to extend the blade assembly against spring resistance into a locked position when fully extended. There is also provided a releasable lock mechanism for the pushrod. Some embodiments of the trocar device have an additional tapered zone proximal to a distal end of a trocar shaft within which slides the pushrod. The trocar device has either a self retaining tubular cannula engaged for delivery upon a trocar shaft, or a self retaining expandable cannula folded and engaged upon a trocar shaft.

The cannula may alternatively be a multi-segmental flexible piece, the segments joined in the center by a geometrically regular network of filaments, the filaments shaped and conjoined in such a way as to enable the segments to be folded and interengaged into a substantially tubular shape with the filaments thereby forming an outwardly collapsible structure having at least two break lines. With this in mind, other geometrical arrangements will occur to those skilled in the art.

In order to fulfill the requirement that an adequately sized cuffed tracheotomy tube can be placed, the cannula is made so that its preferably thin walled quadrisegmental tube will dilate as the cuffed tube is pushed easily through it into the trachea.

The preferred tracheal cannula is preferably made of polypropylene. It is preferably molded in a relatively flat plane with the ends of the quadrisections joined in the center to a network of interconnecting struts or filaments that is stretched and folded up to form a basket weave-like pattern as the sections come together, overlapping like the petals of tulip, to form the percutaneous tube. The extra-corporeal portion of the cannula comes together to form the manipulative tabs on the hub, leaving the cannula segments to form a long tapered, funnel-like throat whose inner surfaces wedge outwardly as the cuffed tube is pushed in. A short cylindrical "keeper", which fits over the assembled sections of the funnel to hold the cannula together, is preferably provided and shaped as a standard 15 mm resuscitator coupling. If placement of a cuffed tube is indicated, the keeper is removed to allow insertion and expansion of the cannula.

This device, described above for use in performing cricothyrotomy, may, with scale and relative dimensions modified, also be used for performing a thoracostomy. A thoracostomy system is also disclosed that utilizes a large bore retractable trocar instead of a needle to decompress the thorax.

Preferably, a safe-ended incision mechanism is provided that is retracted upon entering the chest, thus avoiding the potential for internal injury during deployment. The incision mechanism for this embodiment of the invention directed particularly toward thoracostomy also has two identical single beveled blades that are pivotally mounted for cam action expansion with their cutting edge sides face to face and overlapped at their respective points when fully extended. They also form a delta or "V" shaped edge when extended, with (looking edge on) one half beveled on the left and the other half beveled on the right, so that there is a double thickness, double beveled point in the center generally having a blade sharpness angle that is twice that of either single blade.

The preferred profile of this alternate cutting edge is about a 135° delta shape with a small zone, preferably about 1 mm, at the double thickness, double beveled center of the delta edge. The edge of this small zone is preferably perpendicular to the long axis of the trocar shaft. This slower cutting, less pointed zone is generally the result of an additional grinding step on each blade point that takes off a tiny portion of each sharp blade tip, while leaving the newly ground tip at the same blade sharpness angle as the rest of the blade, but in a new plane slightly skewed with respect to the plane of the cutting edge, and are the preferred safe-ended mechanism referred to above. The shallower delta shape and this safe zone serve to limit the depth and danger of initial penetration, particularly with respect to the danger of damage to underlying internal organs. The rib cage is strong enough to sustain the forces necessary to incise the dense, relatively noncompliant intercostal tissues fixed between the ribs, and to dilate a chest tube channel with this relatively wider, less pointed, slower cutting edge. These intercostal tissues provide sufficient resistance to allow the necessary cleavage forces to be achieved and maintained during sharp dissection.

On the other hand, the highly compliant, soft, rubbery tissues of the underlying internal organs do not provide sufficient resistance (as does the rib cage) to the widely spread axial pressure of the plunging trocar to enable it to penetrate. Preferably, the thick tapered body of the trocar shaft starts only 5 mm behind the leading edge of the extended blade, further adding to the resistance to penetration of soft organs. In addition, this style point prevents accidental engagement and distortion of the blade tip by the superior border of the rib (in case it is bumped) during insertion.

Flattening the V shaped incising edge to about 135° spreads the force of insertion over a wider area and increases the amount of pressure that is needed to start penetration. Since the apex of the blade point is thus closer to the plane of the lateral blade ends, the blade point has to penetrate only about 5 mm to make a complete incision into the chest cavity. In this short distance, the soft underlying internal organs cannot produce enough resistance to the slower cutting delta edge to be punctured or cut. Significantly, the expanded or extended blade mechanism is closed and spring retracted into the trocar shaft at this point by the simple push of a button on the handle of the insertion tool and the trocar has a relatively blunt end throughout the rest of the insertion sequence.

The trocar is then fully inserted and then the trocar shaft is removed to leave in place an included 13 to 14 mm I.D. plastic delivery cannula. The cannula can then manually be directed to the portion of the chest where the chest tube needs to be inserted. The chest tube is then inserted through the cannula, and the cannula is removed.

In the disclosed system the smallest possible surgical lesion is produced in the process of applying any of the devices disclosed, resulting in less post-operative pain and faster healing; the chest tube can be placed with the fewest possible steps in the shortest possible time; and the incision produced will be just large enough to allow relatively easy placement through the incised tissue of a preferred 13-14 mm I.D. delivery cannula that is sized to facilitate installation of a 36 size French chest tube.

In addition, the relatively minimal size of the incision and the dilation of the incision channel by a preferably tapered trocar shaft retains natural tissue resiliency and causes the tissue to close tightly and to directly appose the chest tube after the delivery cannula is withdrawn. This allows a negative intra-thoracic pressure to be reliably maintained without the need for sutures on either side of the chest tube to close gaps around it. If the location of the chest access needs to be changed, the trocar can be easily reassembled and reapplied.

For embodiments intended for thorax and abdomen intubation, there is a tapered extension of the trocar shaft just behind the blades that progressively dilates a relatively smaller incision, and cause the tissues to fit more tightly around the cannula. Preferred devices have an automatic, self-activating, twin-blade incision mechanism blade retractor that is automatically retracting.

Current laparoscopic trocars have safety shields that slide over the sharp trocar tip at the time of penetration to protect against lacerations resulting from deep penetration of the sharp trocar tip. Those designs, however, lack the ability to produce adequate sharp dissection of the tissues during the process of trocar insertion, and require a scalpel incision first.

Although the skin and internal organ characteristics of a pig are quite similar to humans and make it the best non-primate model for testing our device, the nature of the swine rib cage had differences that affected the performance testing of the disclosed trocar. The cross section of the pig rib is more round as compared to the thinner and flatter human rib. As a result the rib cage is somewhat thicker and there is a greater mass of muscle tissue filling in the spaces between the ribs. More importantly, the ribs are closer together. Preferred trocars are dimensioned for humans. As a result animal testing employed a trocar device with a diameter that was larger than the natural space between the ribs of a pig.

For testing, all the trocar shafts had a tapered 9 mm tip and mounted either 9 mm or 13 mm blades thereon. This tapered tip design produces the best wedging effect and easiest possible insertion. Both blade sizes function in this configuration and thus allowed testing of the effect of incision size on insertion ease and tube fit without the variable of two different shaft shapes as initially proposed. Each blade, with a precise pattern of holes and slots, is cut from stainless steel stock using a computer controlled wire electron discharge machining method to assure uniform function of all devices. Both the 13 mm and 9 mm blades and the tapered tip penetrated the skin and intercostal tissue quickly and easily when lubricant was used, but greater force than anticipated was necessary to deflect and separate the ribs as the tapered incision (wound) dilating surfaces on the shaft and cannula were engaged during full insertion. This led to sudden and excessive penetration of the thorax in some early trials. The automatic blade retraction mechanism functioned well however and prevented damage to the lung, even in the worst cases.

The greatest control and easiest insertion is accomplished by using short, sharp trusts to wedge the ribs apart after the skin was penetrated and the tissue dilating section of the trocar cannula under these worst-case penetration conditions. Subsequently an adjustable penetration stop feature was added as well, that was very effective in controlling depth of penetration.

A rocking motion of the trocar is the preferred method of incision through the skin, with the blades expanded and locked. The stop mechanism on the shaft of the Thoracar device is placed to prevent excessive penetration. Stop placement is based on estimated thickness of the chest wall. The trocar is then rapidly moved with a light pumping motion through the subcutaneous tissues, tunneling and entering just superior to the rib for the intercostal space selected. Penetration into the pleural space is accomplished and after the automatic retraction of the blades, the trocar sleeve and blunt shaft are further inserted, and then the shaft retracted to allow expansion of the retention flanges on the cannula.

The 9 mm blades produced the best combination of incision size, ease of insertion and final fit of the chest tube after full deployment and subsequent removal of the delivery cannula. The 13 mm blade versions were not noticeably easier to insert, and the larger incision tended to be looser around the chest tube.

In one thoracostomy device, the sliding tip is made so both sides retract and extend together as a unit. This adds to the symmetry of the sliding tip section and increased the area of tissue engagement to move the tip rearward and initiate the auto retraction cycle. However, testing indicated sometimes inconsistent blade retraction, apparently due to linking of the slide mechanism by tissue impacted into the space between the blades and double slide.

Accordingly in a preferred embodiment, the tip slide mechanism has an asymmetrical, one-side-only moving penetration detector slide. This configuration has less area of tissue engagement for tending to move the slide rearward to set the trigger, but is mechanically much simpler and has very little internal friction. This preferred design has no overlapping cylinders and only two points where the polished steel push rod passes through polished holes during its travel. There are two "speed bumps" (see FIG. 21), on the slide to increase the tendency of the sides of the tip to engage the tissue and urge the slide backwards. The trocar is applied with the slide side down. This applies the resistance encountered in passing over the rib directly to the "speed bumps" on the slide and easily moves and holds it backwards without a noticeable increase in the overall resistance encountered during insertion.

The one-side slide tip trocar preferably has 9 mm blades that are set to project outward about 5 mm from the retracted tip, generally about 2 mm farther ahead than the double slide version. The single slide is preferably and adjustably set to be about 80% retracted to expose as much of the blades as possible. The activator spring mechanism is also adjusted to increase retraction force and to aid with reliable function. There is an extension to the reset button on the top of the handle to ease operation of the blades, especially in case they need to be re-extended and the trigger reset to complete insertion of the trocar. The 5 mm blade setting made the easiest cut of all and the single slide penetration detector functioned flawlessly in testing and automatically retracted the blades every time.

Use of the disclosed trocar virtually eliminates the possibility of inadvertently puncturing deep structures (lung, diaphragm, pericardium, heart), because it's wide V-shaped, twin-blade, retractable incision mechanism is extremely sharp but not pointed and because the blade assembly is retracted immediately after penetration into the chest cavity. The blades are then retracted automatically into the end of the trocar shaft to leave a blunt end (an alternate retraction mechanism is semi-automatic, requiring the push of a button on the handle to release the spring activated retraction mechanism).

The blade at the apex of the trocar is double thickness and shaped like a chisel. The two identical 0.225 mm thick, 17°, single bevel blades, on left, one right, overlap at the tip and are ground to form a 1 mm 34° straight chisel on the end. Though very sharp, the steeply pitched edge greatly increases the area of force application, thus requiring much greater force to achieve penetration. The dense noncompliant tissues fixed between the ribs provide sufficient resistance to allow the necessary cleavage forces to be achieved and maintained during sharp dissection and dilation of the wound channel to insert the cannula. The highly compliant, soft, rubbery tissues of the afore-mentioned internal organs cannot provide sufficient resistance to the widely spread axial pressure of the plunging trocar to enable the chisel point and wide, flat edge to penetrate. The thick tapered body of the trocar shaft starts only 5 mm behind the leading edge, further adding to the resistance to penetration of soft organs.

Installation of the preferred self-retaining delivery cannula in a single stroke prevents the path of insertion into the chest cavity from being lost during the procedure. The end of the thin-walled cannula collapses and flares out as the blunted trocar shaft is pulled from within it. This anchors the cannula lightly within the chest cavity. A conventional chest tube can then be placed through it with no further manipulation of the tissues, whereas the conventional technique requires multiple penetrations and extensive tissue manipulation to insert the tube.

The differences between the very restrictive anatomy of the laryngeal hard structures and the vacuous depths of the chest cavity will allow a thoracostomy trocar to be inserted further during deployment, provided that the end can be made safe after initial penetration. Thus a preferred embodiment adds a tapered extension of the trocar shaft just behind a relatively smaller set of blades, the tapered extension progressively dilating the smaller resulting incision and thus causing the tissues to fit more tightly around the cannula and result in a smaller scar. This thin-walled, single-use, collapsing polypropylene part is reliably reproduces is by injection molding. Each part is permanently deformed during insertion/application. This version has a preferred 13 mm shaft that has a section on the end which tapers slowly down to 9 mm and has two 9 mm blades (rather than the 13 mm blades of an alternate version). A self-retaining 13 mm I.D. delivery cannula is provided to fit it on either version, depending on how the collapsing struts on the end are unfolded after it is made. Each cannula preferably has an easily adjustable penetration control ring gripping the outer cannula circumference.

The skin and body wall are well designed to resist puncture and penetration into body cavities. It will be appreciated that placement of a large (>10 mm O.D.) trocar through the skin into a body cavity (trachea, thorax, abdomen) is extremely difficult, if not impossible, if an adequate surgical incision and sharp dissection of the underlying tissue layers is not accomplished prior to insertion. Extensive testing of many cutting tip and blade designs demonstrates that any blade that is no wider than the inside diameter of the cannula mounted on the trocar shaft and that is merely pushed straight in without any substantial lateral motion will not make an incision that is wide enough to allow a short, straight cannula to be pushed through the body wall without excessive force and without extreme danger of over penetration and mutilation of underlying tissues, no matter what the shape or length of the blade. In addition, any uncontrolled lateral motion of a pointed blade during incision into the body cavity can lacerate organs which may be immediately underlying. The retractable cutting mechanism disclosed herein, that preferably makes an incision about twice as wide as the trocar shaft itself, enables easy and reliable insertion of the trocar. Tests demonstrate that even concerted effort to penetrate a hyper-inflated lung directly after the chest was penetrated was unsuccessful in doing so, even with multiple straight thrusts of the disclosed trocar.

Only with adequate sharp surgical incision of the skin and underlying tissues can insertion of a large bore (10 mm+) percutaneous tube be easily, safely and reliably accomplished. Gentle, progressive dilation of the incision is desirable for installation of the tube. The disclosed design accomplishes incision, dilation and installation in one motion, one step, with one instrument, with anchoring and gentle retention of the preferred inserter sleeve/breathing tube combination accomplished as the shaft is withdrawn from within the cannula.

The tapered dilator segment of the trocar shaft is self-centering and insures axial force application during insertion, to prevent unwanted lateral motion and to prevent inadvertent deep organ penetration. A preferably built-in tapered wound dilator, provided in varying sizes, transfers dilating forces from the tip of the trocar shaft to the sides of the cannula struts, due at least in part to preferred inletting of the collapsible cannula struts onto the trocar shaft. The resulting configuration locks the cannula onto the shaft and enables out folding of the self-retaining mechanism during withdrawal of the shaft.

For other applications, the retractable twin-bladed incision mechanism can be made in a large or miniature scale and can also be used to deliver tubes that are not expandable or are not self-retaining. The preferred spring loaded rod linkage which extends and retracts the blades can be made to any desired length and can be both flexible and activated remotely, as through a surgical endoscope or catheter. Therefore, without departing from the scope of the invention, the device could be modified by those skilled in the art for endoscopic microsurgical insertion of tubes or shunts which require a precise, controlled puncture into a body cavity.

While it is counterintuitive that the chest wall could be penetrated by a trocar with widely spread, razor-sharp blades without incurring the risk of lacerating internal organs, this is nonetheless the effect and benefit of the disclosed retractable trocar technology. Its safety and effectiveness have been demonstrated in a realistic animal model. It is believed that flattening the V-shaped incising edge, which is composed of two identical 0.225 mm thick, single beveled blades assembled face to face, to 135°, as compared to the 100° delta point on Cricar brand trocar previously disclosed, and grinding a tiny chisel-like edge at the double-thickness, double-beveled blade apex, spreads the force of insertion over a wider area and increases the amount of pressure that is needed to start penetration.

The disclosed trocar is thus held like a screw driver, with the handle pulled tightly against the palm and the blade aligned parallel with the ribs. The skin is stretched up slightly with the opposite hand and the trocar is pushed slowly and firmly, over the top of the rib, straight into the chest cavity. The two-part blade makes a precise incision that is sized to match the circumference of the self-retaining cannula and thus produces the proper amount of sharp dissection to allow gently, easy insertion of the trocar. An abrupt drop in tissue resistance as the trocar "pops" into the chest cavity and the sound of air or sight of blood flowing through grooves in the trocar shaft indicate full penetration. Lateral or slicing motions are NOT used.

Since the blade apex is close to the plane of the lateral blade ends, the disclosed blade point has to penetrate only about 5 mm to make a complete incision into the chest cavity. In this shout distance, the highly compliant, soft, rubbery tissues of underlying internal organs do not provide sufficient counter-force (whereas the rib cage does) to the widely spread axial pressure of the slower cutting, safe-ended delta edge on the plunging trocar to enable it to penetrate them. In our initial sheep cadaver test, described herein, we were able to make multiple thrusts >100 mm directly against the hyper-inflated lung without damage. The thick, tapered body of the trocar shaft starts only 5 mm behind the leading edge of the extended blade, further adding to the resistance to penetration of soft organs. Significantly, the expanded double-bladed mechanism is closed and spring-retracted, in one embodiment, back into the trocar shaft at this point by the simple push of a button on the handle to leave the trocar with a blunt end through the rest of the cannula installation sequence.

The built-in, tapered incision (wound) dilator transfers dilating forces from the tip of the trocar shaft to the sides of the cannula struts due to the inletting of the collapsible cannula struts onto the trocar shaft. The resulting configuration locks the cannula onto the shaft and enables outfolding of the self-retaining mechanism to lightly anchor the cannula as the shaft is withdrawn. The Thoracar brand disclosed trocar accomplishes safe, precise incision, gentle dilation, installation and anchorage of its delivery cannula in a single stroke, with one step, and one instrument.

An additional safety feature is incorporated into preferred disclosed devices. A two-stage trigger mechanism in the end of the trocar shaft is set as the trocar is advanced through the chest wall and is then released automatically to retract the blades at the instant the tip penetrates into the chest cavity. This reduces the chance of error and further simplifies the procedure by eliminating a step and, most importantly, eliminating any possibility of inadvertent internal organ laceration.

The disclosed device makes the smallest possible surgical lesion necessary to allow easy placement of a 14 mm O.D. delivery cannula sized for installation of a 36 French chest tube; installation of a self-retaining delivery cannula in a single stroke prevents the path of insertion into the chest cavity from being lost during the procedure; the device allows placement of the chest tube with the fewest possible steps in the shortest possible time; and use of the device does not puncture or lacerate underlying organs.

BRIEF DESCRIPTION OF THE DRAWINGS

FIGS. 8a-c are a partial sectional schematic view of the device shown in FIG. 7.

FIG. 9 is a detail of an alternate embodiment of the device shown in FIG. 7.

FIG. 10 is an alternate embodiment of the cannula casting of the device shown in FIG. 7.

FIGS. 11a-b are schematic sectional views of the flutter valve aspect of the invention.

FIG. 27 is a detail perspective end view of a reset button aspect of the device shown in FIG. 14.

FIG. 28 is a detail side view of a cannula release aspect of the device shown in FIG. 14.

FIG. 29 is an alternate detail side view of a cannula release aspect of the device shown in FIG. 14.

FIG. 30 is an alternate detail side view of a cannula release aspect of the device shown in FIG. 14.

FIG. 31 is a detail perspective view of a collapsing struts aspect of the device shown in FIG. 14.

FIG. 32 is an alternate detail perspective view of a collapsing struts aspect of the device shown in FIG. 14.

BEST MODE OF CARRYING OUT THE INVENTION

Figure 1:
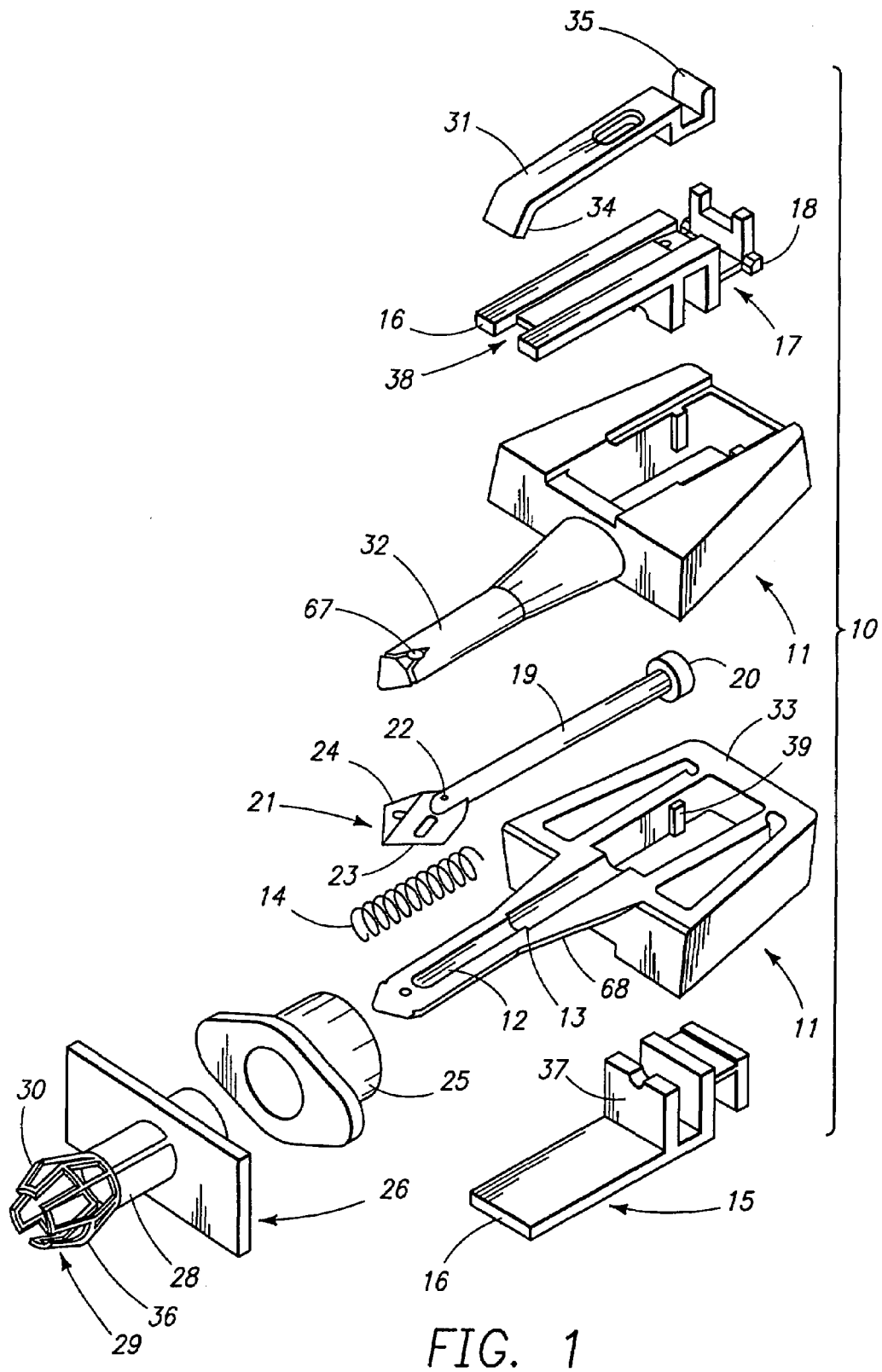
FIG. 1 is an exploded perspective view of a cricothyrotomy embodiment of the invention.

Turning now to the drawings, the invention will be described in a preferred embodiment by reference to the drawings and to the numerals of the drawing figures wherein like numbers indicate like parts. In this specification, the term proximal refers to a position relatively closer to the operator, and distal refers to a position relatively farther from the operator.

FIG. 1 is an exploded perspective view of a cricothyrotomy embodiment 10 of the invention. Blade assembly 21, preferably consisting of two substantially identically formed stainless steel blades 24, one flipped over and both overlapped edge to edge, both pivotally mounted for co-rotation upon axis pin 22, pin 22 preferably a light press fit within an appropriate pin bore (not shown) in the distal end of rod 19. Each blade edge 43 (see also FIGS. 2, 3, 12 & 13) is precision ground in a single bevel to a preferred edge angle 62 of 17°. Each blade 24 for this embodiment is preferably 0.2 mm thick by 7.2 mm wide (and about twice that long), and made from chromium stainless steel, strip type 302, full hard, C-40/45. Those skilled in the art will appreciate that other blade thicknesses and widths and materials might be chosen for blades 24 without departing from the scope of the invention.

Figure 12A:
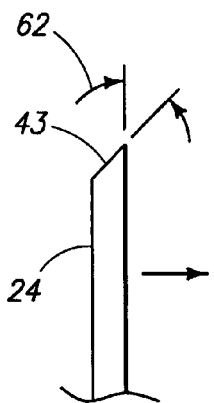
FIGS. 12a-c are partial side details of the blade edges of the blades shown in FIG. 2.
Figure 12C:
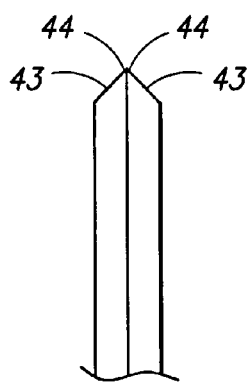
Figure 12B:
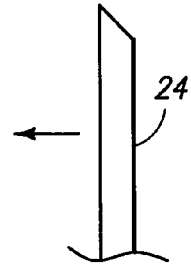
Figure 13B:
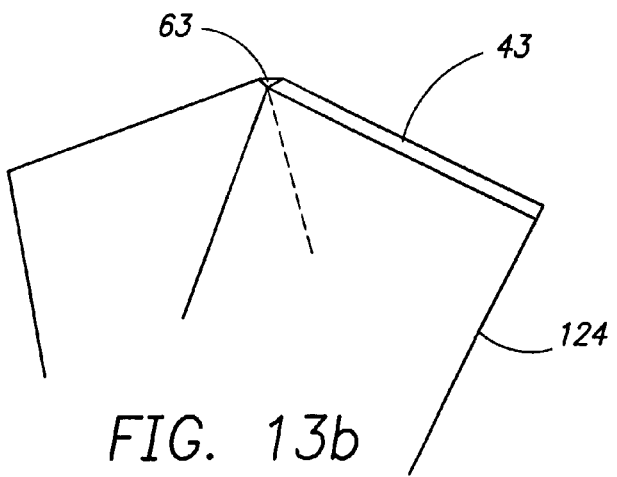

Each of the blades 24 has a blade angle 45 (FIG. 3b) at blade point 44 that is preferably about 65° in this embodiment at this point. At the apex of blade assembly 21 is delta point 46, where the overlapping blade points 44, upon full extension, preferably form for that region of blade assembly 21 a double blade thickness of 0.4 mm, with a preferred combined edge angle of 34°, roughly shaped like a chisel (FIG. 12c).

Rod head 20 rides engaged within the facing slots of mated rod retainer halves 15 and 17, so that in operation rod 19 and retainer halves 15 and 17 with their distal safety tabs 16 move as a unit, with rod 19 slidably engaged within rod channel 12 of mated body halves 11. Trocar 32 depends distally from handle 33, and channel 12 lies within trocar 32. Edges of trocar 32, and distal edges of handle 33 are preferably beveled at approximately 45 to form, when body halves 11 are mated, a flute 68 about 1 mm in depth all the way around the trocar and out the handle for release of air upon penetration into the body cavity. Trocar shaft 32 is desirably slightly radiused at its tip. Facet pair 67 near preferred conical tip of trocar 32 are formed by removing some of the conical shoulder to form two planar zones of somewhat slower wedging action than the wedging action of the rest of the conical angle. These facets 67 thus result in somewhat easier insertion start of trocar 32 through a body wall.

Figure 4C:
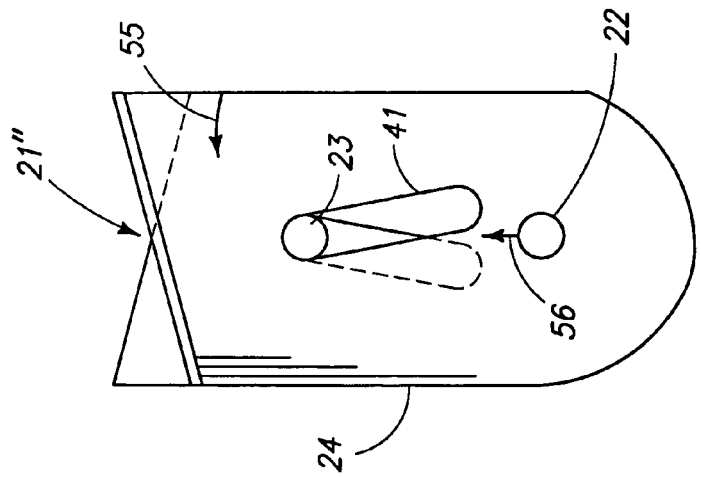
FIGS. 4a-c are plan view schematic sequences of the blades shown in FIG. 2.
Figure 4B:
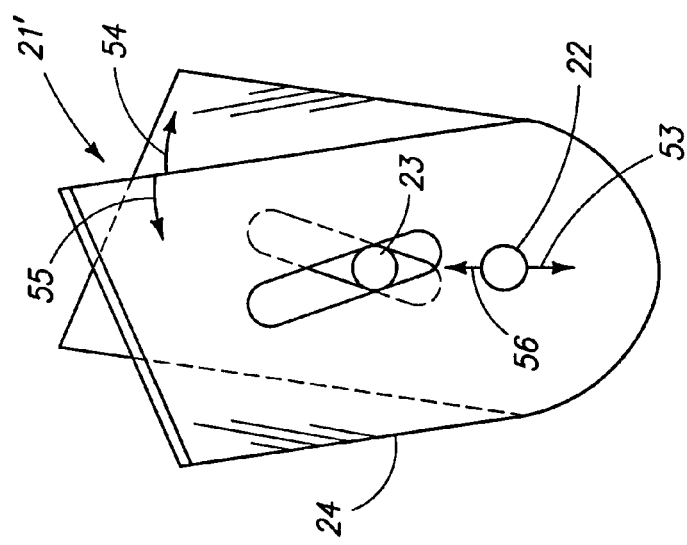
Figure 4A:
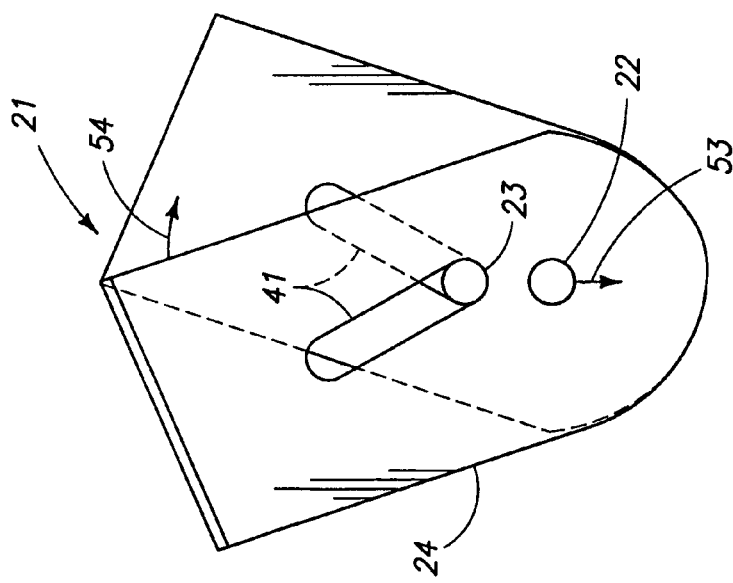

Cam pin 23 is engaged within both cam slots 41 of blades 24, and is also preferably a light press fit in an appropriate pin bore (not shown) in trocar halves 32, about one trocar's width back from the tip of trocar 32, such that, as rod 19 moves forward and back with its mounted blade assembly 21, cam pin 23 remains stationary relative to trocar 32, but can be seen as relatively slidable with respect to cam slots 41 (see FIG. 4a-c). Cam pin 23 is preferably a rolled steel type of pin, and is positioned as close as possible to tip of trocar 32 without lying in any of the conical or faceted portion of the tip. Positioning further back will not disable the functioning of the device, but will make for a more aggressive (less leveraged) blade opening, and will generally require a proportionately longer blade length, together with a roughly proportionately heavier spring. It is of course the cam slots that move with the blade assembly, and not the cam pin, but some discussion and illustration may make more ready sense if the cam pin is viewed as relatively movable with respect to the cam slots.

Spring 14 is coiled around rod 19 and is seated in spring seat 13 at a point within channel 12. The other end of spring 14 is engaged by spring thrust face 37 of retainer halves 15&17, such that as rod 19 (with its retainer halves) is moved forward distally through channel 12, it does so against the urging of spring 14, compressing the spring and loading retainer lock tab 18 on retainer half 17 against retainer lock bar 39 (see FIGS. 5a-b) in handle 33. Desired spring force from spring 14 has not been quantified but selection of a stock spring of sufficient force to effectively retract blade assembly 21 should present no difficulty to the person skilled in the art.

Auto release bar 31 is mounted upon retainer half 17 so that release tab 34 slidably fits within tab slot 38 in safety tab 16, and blade lock release 35 fits within a corresponding slot at the proximal end of retainer 17. Retainer halves 15&17 are mated and slidably engaged within handle 33 in such a way that their fit within handle 33 is somewhat loose, allowing retainer 17, 15 and release bar 31 to pivot with a slight rocking motion about a distal portion of the body material 11 of handle 33 (see pivot point reference 58 and body material 11 in FIG. 5b).

During assembly of device 10, and after the mating referred to above, and with rod 19 fully back (so blades are not extended), coupling 25 is assembled onto the proximal end of cannula assembly 26, which is then slid onto a proximal portion of trocar 32. Cannula assembly includes tabs 27, cannula 28 and collapsible strut network 29. Network 29 includes a number of struts 30 and living hinges 36 (see FIG. 6a-e). It should be noted that in FIG. 1, strut network 29 is shown as partly collapsed, though that is not its typical state at assembly stage. When assembled, much of network 29 is enmeshed within the preferably molded in progressive inletting 40 (FIG. 6e) of the distal end of trocar 32 so that network struts 30 present little if any added resistance to body insertion of trocar 32, and are thus not prematurely collapsed upon insertion. Inletting 40 is progressive in that it is fully as deep at its distal-most portion as the network struts 30 are thick (same thickness as cannula, approximately 1 mm), but tapers to ever shallower inletting until at the proximal-most end of the inletting zone there is no inletting depth at all.

Figures 2, 3A, 3B:
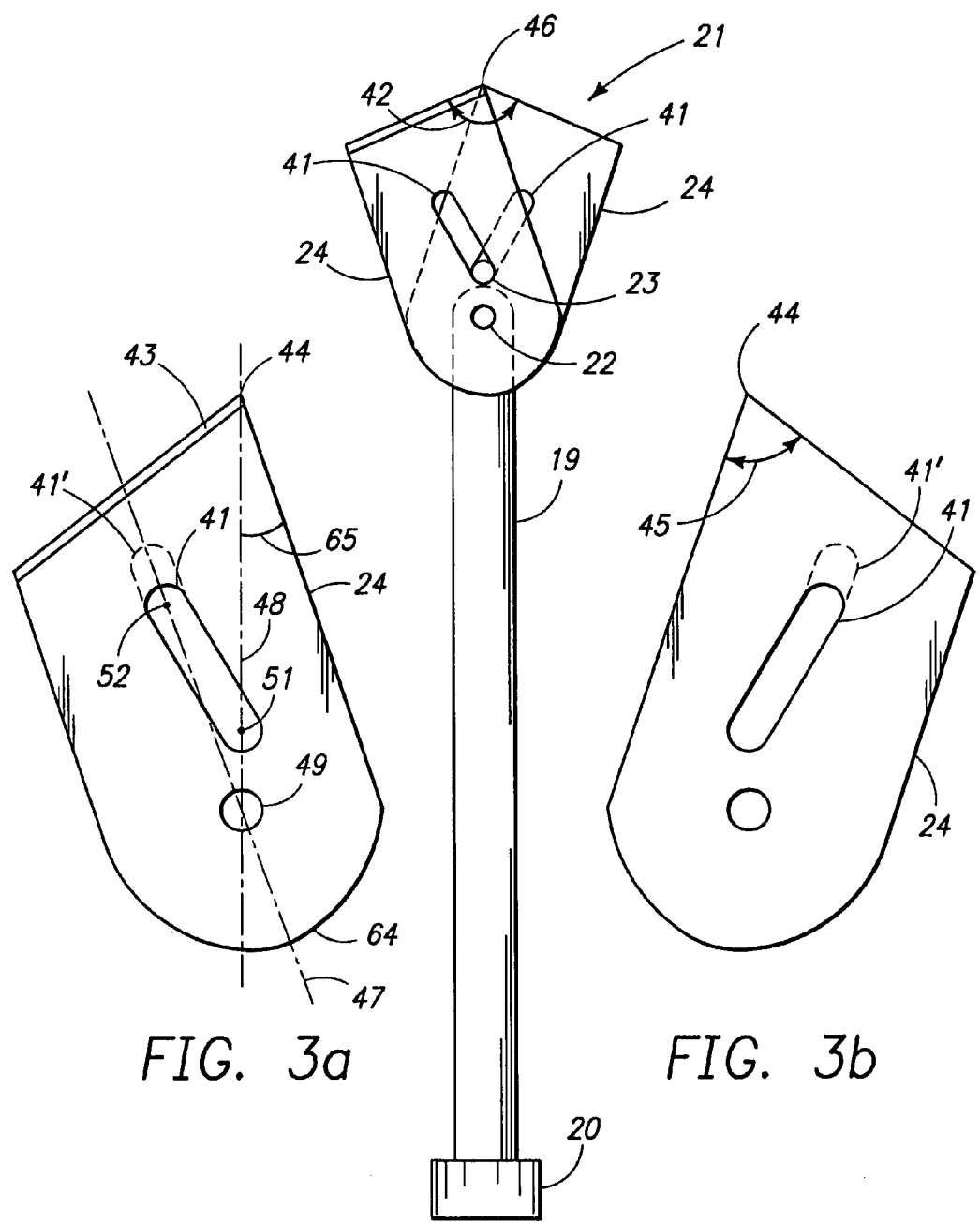
FIG. 2 is a detail partial plan view of a preferred blade mechanism of the invention.
FIGS. 3a-b are further plan view details of the blades shown in FIG. 2.

FIG. 2 is a detail partial plan view of the novel blade mechanism of the invention. This is a preferred mechanism, regardless of trocar embodiment; this discussion will apply for the most part to both classes of trocar disclosed herein, though reference numerals refer generally to the embodiment of FIG. 1; like parts for the embodiment of FIGS. 7 & 8 have like part numbers, with FIG. 7 having a 100 series numbers. Blades 24 are pivotally mounted on pivot pin 22 pressed into rod 19; blades 24 may generally pivot anywhere from a fully closed (retracted) engagement with each other, where the entire blades 24 are substantially overlapped (FIG. 4a) to a fully open (extended) engagement with each other, where along blade edges 43 only blade points 44 are overlapped (FIG. 2 and FIG. 4c), to anywhere in between (FIG. 4b). Fully open blades form a combined leading blade edge having a delta point 46, and a delta angle 42. When fully extended, blade assembly 21 has a blade delta angle 42 of about 95° to 100°.

As mentioned above, each blade 24 in blade assembly 21 is substantially identical to the other; they are preferably cut or stamped from the same specifications and are sharpened in the same manner, and on the same side. Only during assembly one is reversed with respect to the other and placed face to face as it where, or edge to edge, so that their respective blade edges 43 are touching at least at one or more points. Thus cam slots 41 that were identical at manufacture are now aligned in different directions (FIGS. 3a-b). Thus, with cam pin 23 fixed in the end of trocar 32 (not shown), it can be visualized that as rod 19 moves forward or back within trocar 32 blades 24 will be cammed open or closed with respect to each other (see FIGS. 4a-c) by the action of reciprocal cam slots 41 against relatively stationary cam pin 23.

As illustrated in FIGS. 3a-b, a number of variables combine to determine delta angle 42, including blade 24 width and length, relative positioning of blade axis pin bore 49 in heel 64 of blade 24, and blade angle 45. Heel 64 is preferably radiuses so that all points on the circumference of heel 64 are equidistant from the center of pin bore 49 (though other heel radius/pin center relationships may be made to serve as well). Top center 52 of cam slot 41 and the center of pin bore 49 are preferably aligned along a line 47 marking the longitudinal center of blade 24. Bottom center 51 of cam slot 41 and the center of pin bore 49 are preferably aligned along a line 48 between blade point 44 and pin bore 49 center. For purposes of estimation of delta angle 42, twice an angle 65 formed by blade side and line 48 may be deducted from twice blade angle 45. Optional cam slot extensions 41' (dotted lines) are doglegged back along line 47, and provide the optional capacity to fully withdraw blade assembly 21 into trocar 32. To best accommodate this optional feature, an extension of blade length of about the same length as the slot extension is desirable.

In this embodiment, cam slots 41 are preferably 0.468 inches in width (approximately the same as the diameter of cam pin 23), and 0.165 inches in length from top center 52 to bottom center 51. Cam slot 41 is preferably offset from line 47 by an angle of 10°, with top center 52 positioned 0.250 inches distal to center of pin bore 49. In other embodiments, whether larger blades and blade assemblies or smaller, dimensions are generally proportional to those described above, except notably for blade angle which may vary as disclosed herein and edge angle which generally does not change with blade size. Thus for example a blade twice as wide will generally be about twice as long, and other dimensions disclosed above also about twice as long.

With that in mind, and with the above instructive disclosure, those skilled in the art will be able to devise variations in blade delta angle 42, bearing in mind that, for any given set of blade width and height and relative pin bore positioning, angle 65 will not vary, and delta angle changes will depend on blade angle changes.

FIGS. 4a-c are plan view schematic sequences of the blades shown in FIG. 2. In 4a, blade assembly 21 has blades 24 are fully open, cam pin 23 is relatively stationary in bottom center of both cam slots 41, and pivot pin 22 in rod 19 (not shown) engaging both blades is withdrawn proximally in the direction indicated by arrow 53, causing blade 24 to move in the direction indicated by arrow 54 to begin greater overlap of the other blade. In 4b, blade assembly 21', pin 22 can move further in direction 53 to further move blade 24 in direction 54, or it can move back along arrow 56 to move blade 24 along arrow 55. In 4c, blade assembly 21", blade 24 having moved along arrow 54 to nearly fully overlap the other blade, pin 22 can now only move back along arrow 56 to move blade 24 back along arrow 55. Note that as pin 22 is withdrawn proximally (toward bottom of FIG. 4), cam pin 23 remains relatively stationary, but the entire blade assembly move further back (lower) progressing from 21 to 21' to 21". It is this action that withdraws or retracts the blade assembly, while at the same time closing it.

Figure 5A:
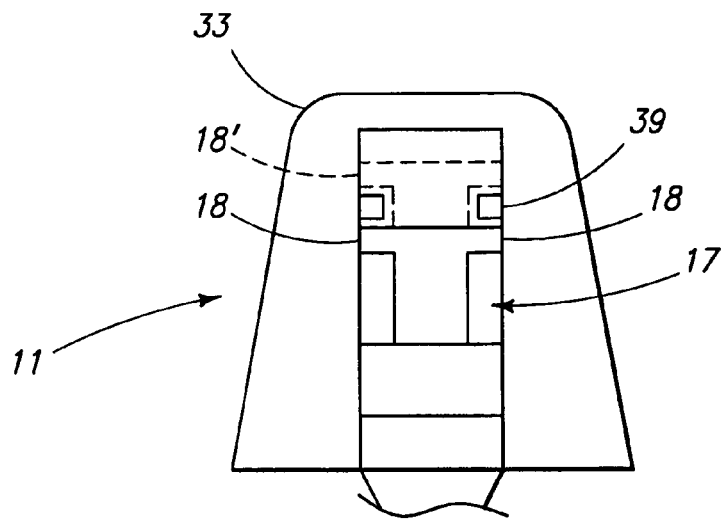
FIGS. 5a-b are detail partial sectional views of the blade lock and spring retraction mechanism of the device shown in FIG. 1.
Figure 5B:
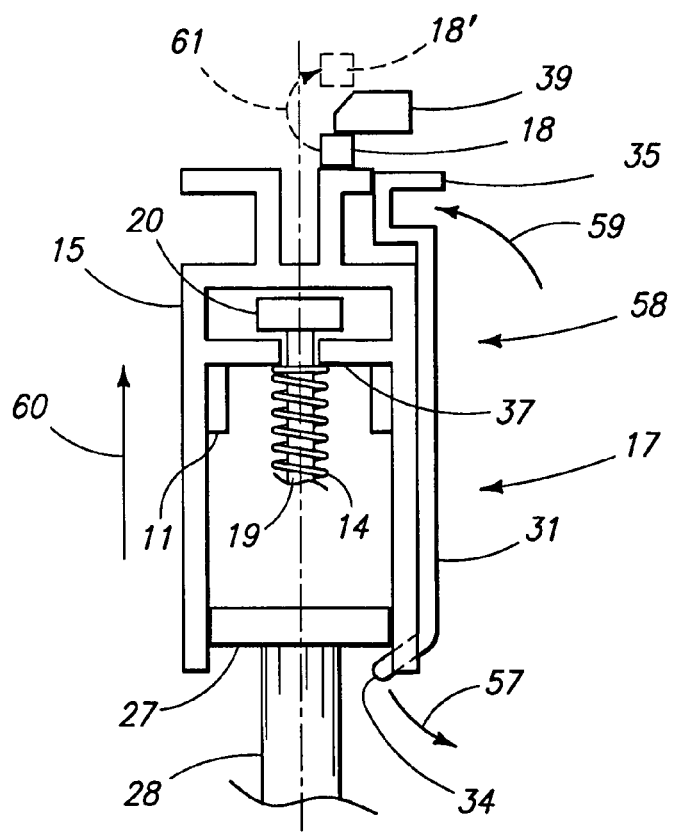

FIGS. 5a-b are detail partial sectional views of the blade lock and spring retraction mechanism of the device shown in FIG. 1. To extend and lock blade assembly 21 in its extended or open position, retainer assembly 15, 17 is grasped and moved distally until lock tab 18 is caught and held in the position illustrated, just distal of lock bar 39. This can be seen from two views in both 5a and 5b. Lock tabs 18 are preferably paired and symmetrical, as are lock bars 39. Lock bar 39 is desirably radiuses approximately as shown to facilitate tab 18 sliding around bar 39 as rod 19 is extended distally. Tabs 18 are required to move slightly around bar 39 to achieve a locked and extended position, and this is facilitated by the previously mentioned loose fit of retainer 15, 17 within body 11.

In the process of advancing retainer 15, 17 distally, spring 14 is compressed and exerts a load tending to restore rod 19 to its unloaded proximal position in the direction of arrow 60. This may be released in one of two ways. Lock release 35 may be pressed, causing the retainer assembly to rock slightly in the direction of arrow 59 around a pivot point indicated approximately by reference mark 58 at the distal edge of body portion 11, so that tab 18 is impelled by spring 14 to travel roughly in the path indicated by dotted arrow 61 in 5b to end up at 18', thus releasing the lock and allowing spring 14 to withdraw retainer 15, 17 and rod 19, and with them the blade assembly to retract and close the blades. Or, if the blades have not been earlier withdrawn prior to an attempt to withdraw trocar shaft 32 from cannula 28, tab 34 will encounter cannula tab 27 and be influenced in the direction of arrow 57, as the trocar shaft is withdrawn. Since release bar 31 is mounted on retainer half 17, rocking movement of tab 34 imparts the same rocking movement to the retainer as pressing release 35, and the unlock and retraction occurs as described above, thus automatically retracting the blades to prevent damage to the cannula from having inadvertently left them open.

Figure 6A:
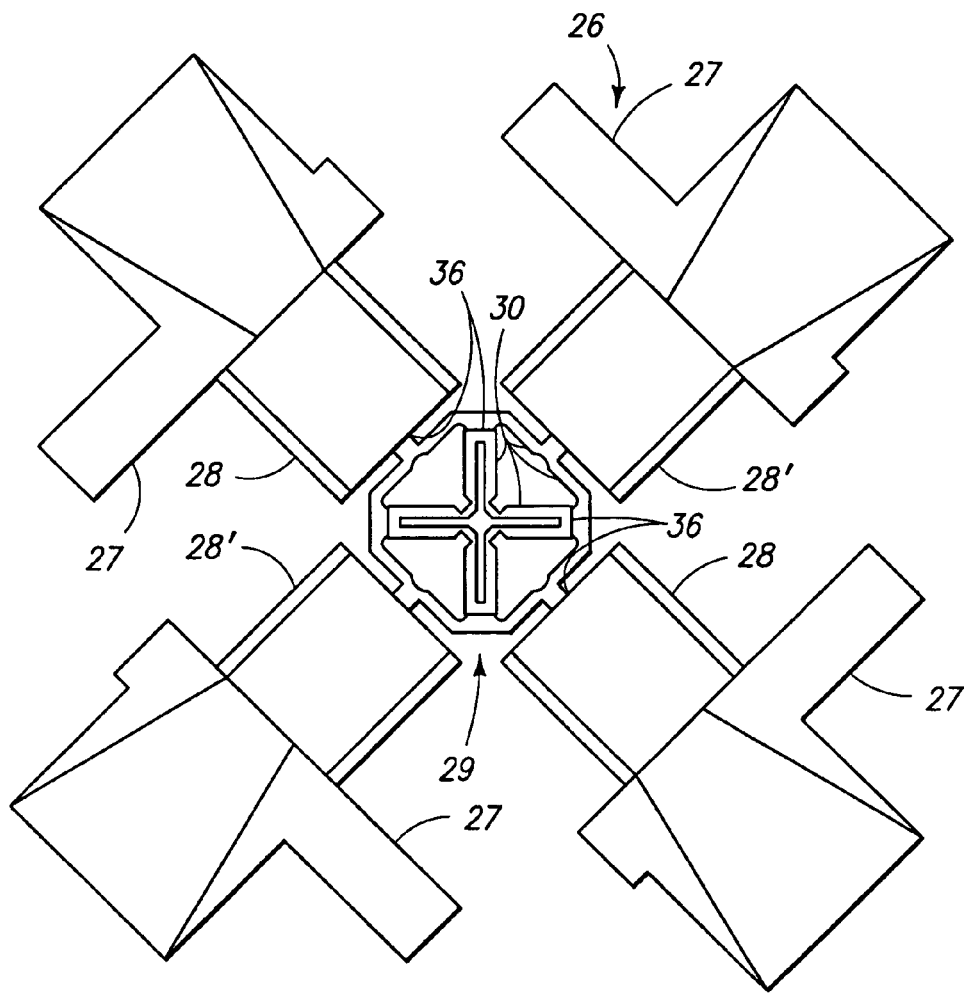
FIGS. 6a-e are plan, side and sectional views of an preferred quadrisegmental cannula shown in FIG. 1, shown first as molded and then as assembled.
Figure 6E:
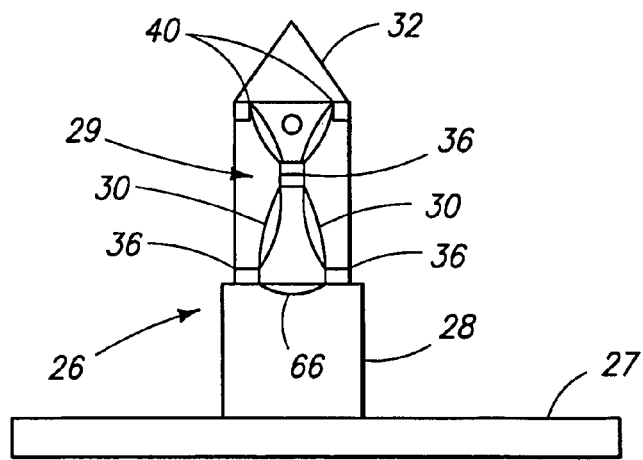
Figure 6B:
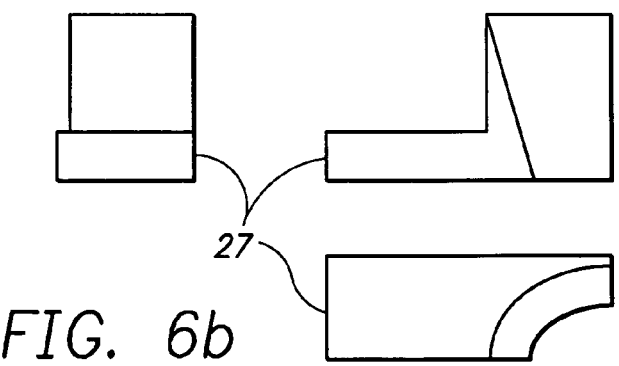
Figure 6C:
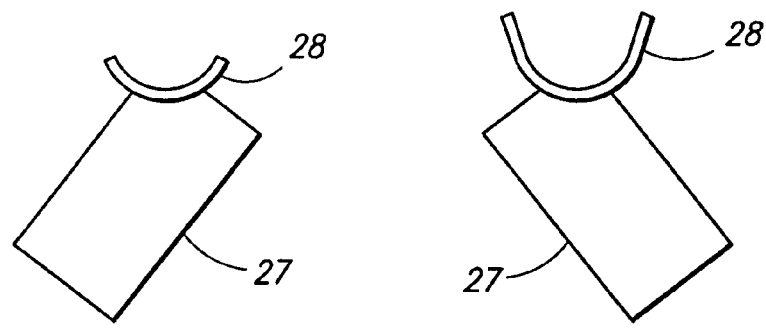

FIGS. 6a-e are views of an preferred quadrisegmental cannula 26 shown in FIG. 1, shown first in plan view as molded in 6a and then in side view as assembled and mounted on trocar in 6e. Cannula assembly 26 is actually preferably a single plastic injection molded piece, shown in plan view in FIG. 6a. Assembly 26 has four segments 27 that, when appropriately folded and assembled, form cannula 28 and cannula tabs 27. Each segment 27 is substantially identical, while portions 28 and 28' differ in that cannula segments 28 are greater in diameter than segments 28', so that when they are folded and assembled, with two segments 28' inside segments 28, the cannula 28 is double walled, but expandable. Tab segments 27 also preferably form a funnel shaped opening, with ¼ of the funnel in each segment. FIG. 6b illustrates, clockwise from upper left, a narrow end view, a broad end view, and a down-the-funnel view of each segment in the molded piece. FIG. 6c shows cannula segment end views of the smaller cannula segment (left) and the larger cannula segment (right).

The central portion of the molded piece in 6a is what will become, with folding and some stretching into the plane of the page of the figure, strut network 29 of cannula assembly 26. Note the presence of struts 30 and living hinges 36 in network 29. Living hinges are formed by generally stenotic regions along a network of struts, with one side of each such stenotic having a scribed or molded in line (not shown) along which the material may be more readily folded. In FIG. 6a these hinge lines are on the back of the part (back side of drawing) along the lines generally indicated by the numerals 36. Note that each strut 30 is also desirably separated from each other and from the living hinges 36 by intervening regions where the material is either also stenotic or angled substantially away from an adjoining strut structure. These stenoses and angles all facilitate the folding of the network necessary to change its shape from flat (6a) to generally conform to the shape of the trocar (6e). As the shape is changed, the stenoses and angles generally experience plastic deformation, while the struts 30 generally do not.

Figure 6D:
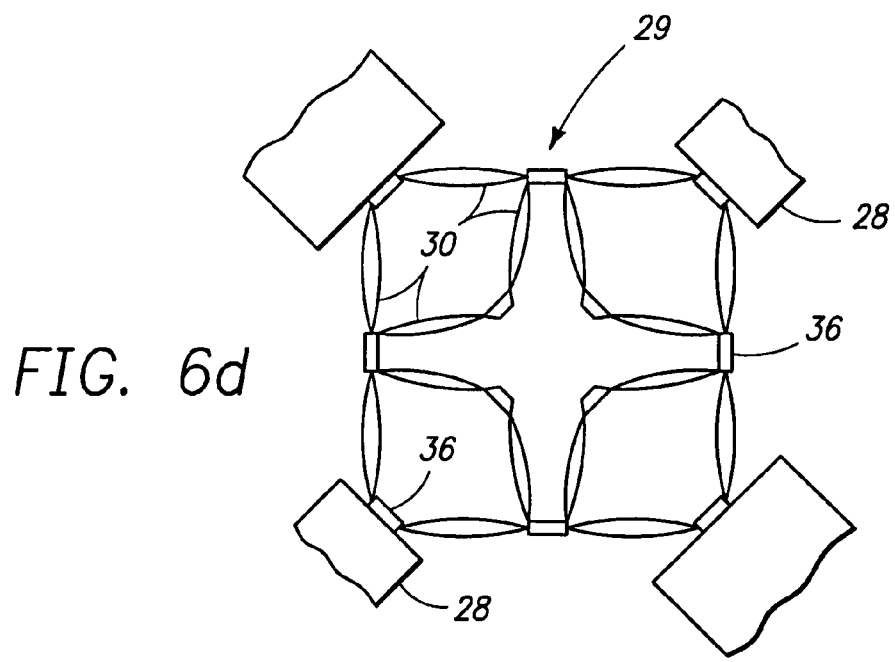

During the assembly folding, part 26 generally passes through a partially folded stage shown in FIG. 6d in which the generally octagonal shape of part 26 in 6a becomes (in plan view) the roughly square shape in 6d. In this view, what are intended eventually as the distal-most struts in the center of network 29 are already pulled out of the plane of the figure, and all of the stenoses and angles have experienced some deformation. The final cannula assembly 26 shape is shown in 6e (with cannula segments 28 and 28' conjoined to the double wall structure referred to above, and the tab and funnel segments 27 fully abutted) with struts 30 and hinges 36 progressively set into inletting 40 in trocar shaft 32. As an additional preferred aid to insertion without hanging up any of the cannula struts, bevel 66 is relieved in the cannula shoulder just proximal of strut network 29. It will be appreciated that, while this structure is shown with what will be seen as two sets of break lines (for eventual collapse), generally along two trocar circumferences determined by two hinge sets, additional break lines formed from hinges as disclosed, or the like, may also be provided without departing from the scope of the invention.

FIGS. 7a-d and 8a-c are photos and partial sectional drawings of the thoracostomy device 100 disclosed. Blade assembly 121, except for certain dimensions and features, is nearly identical to blade assembly 21 for the cricothyrotomy embodiment. Thus blade assembly 121 preferably also consists of two substantially identical overlapped edge to edge stainless steel blades 124, both pivotally mounted for corotation upon axis pin 22, pin 22 preferably a light press fit within an appropriate pin bore (not shown) in the distal end of rod 119. Likewise, each blade edge 43 (see also FIGS. 2, 3, 12 & 13) is precision ground in a single bevel to a preferred edge angle 62 of 17°. Each blade 124 for this embodiment is preferably 0.225 mm thick by 9 mm (in one embodiment, and 13 mm in another) wide, and approximately twice that long. Those skilled in the art will appreciate that other blade thicknesses, lengths and widths and materials might be chosen for blades 124 without departing from the scope of the invention.

Each of the blades 124 has a blade angle 45 (FIG. 3b) at blade point 44 that is preferably about 85° in this embodiment at this point. At the apex of blade assembly 21 is delta point 46, where the overlapping blade points 44, upon full extension, preferably form for that region of blade assembly 121 a double blade thickness of 0.450 mm, with a preferred combined edge angle of 34°, roughly shaped like a chisel (FIG. 12c). When fully extended, blade assembly 121 preferably has a blade delta angle 42 of about 130° to 135°.

Trocar 132 has its own progressive inletting 140 (like inletting 40 described above) to accommodate and receive cannula 128, with its own style of struts 130 and hinges 136 and bevel 166 (FIG. 10—shown as preferred variant 13 mm I.D. 'tapered' version of cannula, molded with network 129 already partially tapered—straight cylindrical cannula and network version shown in FIG. 7a-d). Note presence of two lines of hinges (see especially in FIG. 7b, c, d); as above, there may be more than two lines ('break lines') of hinges without departing from the scope of the invention. Trocar 132 also has tip facets 167 to make an easier insertion start, as discussed for device 10 under FIG. 1. Inside trocar 132 is channel 112, within which rod 119 is slidably engaged. Rod 119 extends back into handle 133, preferably comprised of body halves 111. Rod head 120, with thrust washer 137 receives the spring load of spring 114 seated upon washer 113. Rod head 120 has a channel 123 to slidably receive lock bar 139.

Rotating the view in 8a ninety degrees and again looking in section, the operation of lock bar 139 with rod head 120 and key holes 122 may be seen. Narrow portions of lock bar 139 provide relief 135, so that in the position illustrated, reliefs 135 are free to slide in through out and along the length of keyway 122 let into both sides of handle 133. When rod 119 is urged forward by thumb and finger pressure on button 134 and nub 118, spring pressure is increased and the blades extend and open. At the point of maximum extension, nub 118 is positioned over the wide portion of keyway 122 and, with some balance on button 134 so wide part of lock bar 139 just inside the button side relief 135 can be urged simultaneously into its wide part of the other keyway 122, nub 118 may be lightly pressed in the direction of arrow 153 into keyway 122, where it serves as a lock to hold the blades extended. To release the blades for spring loaded retraction, only button 134 need be pressed in the direction of arrow 154, thus presenting again the relief portions of lock bar 139 to keyway 122 so that rod head and rod may freely slide backward under the urging of spring 114.

Figure 7A:
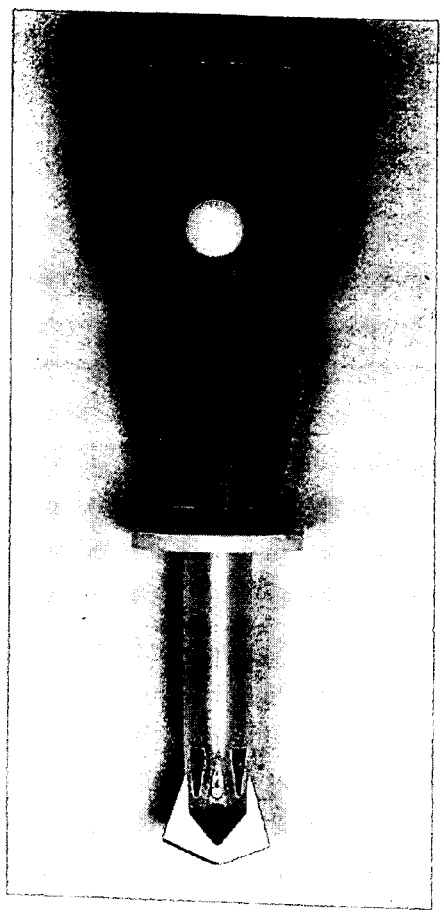
FIGS. 7a-d are photographs of an alternate thoracostomy embodiment of the invention, in sequence of operation.
Figure 7B:
Figure 7C:

FIG. 9 shows an alternate embodiment of the device shown in FIG. 7a. In this embodiment, trocar 132 is preferably a wider 13 mm trocar (carrying a 13 mm cannula, shown separately in FIG. 10), but with an optional tapered extension 141 that tapers from 13 to 9 mm. This allows a 9 mm paired blade assembly for a relatively smaller incision than with a full 13 mm blade set, but provides a tapered expansion zone to push open the incised tube channel in the body tissue to a full 13 mm opening to receive the wider cannula.

FIGS. 11a-b are schematic sectional views of the optional flutter valve aspect of the invention. A silicone plastic, flat sleeve 143, shaped like a duck call reed, when attached 142 to the cannula hub 127, will act as a one way flutter valve to let air and body fluids pass out of the chest cavity, while admitting no air or other matter into the cavity (11a). This valve 143 may optionally be assembled with cannula 128, by attaching a valve base to the hub (such as by ultrasonic or electronic welding), adhesive, or the like), fitting the trocar 132 end into the sleeve end, and then pushing the sleeve into the cannula with the trocar (11b). Upon withdrawal of the trocar, the sleeve is deployed to become the one way exit valve.

FIGS. 12a-c and 13a-b are partial plan details of the overlapped blade points of the blade assemblies of both devices 10 and 100, illustrating the optional common scheme for creating a safe ended zone on the delta point 46 of the extended blades. As described and discussed above, for most of the blade profile of the fully extended blades, there is presented only a single bevel 17° edge, one left, one right (12a, 12b)—very sharp. This serves well for incision generally, but can lead to dangerous over insertion, as discussed. The slight but significant blade overlap at the points (FIG. 12c), without further modification produces a narrow safe zone of relative blade bluntness, in that the cutting edge for this region only is effectively 34°, not just 17°. Optionally, this zone may be widened by grinding each blade point, after grinding the 17° edge, with a second, slightly offset grind, preferably also 17° (though other grind angles may serve as well to produce relatively blunt or even blunter zone). This second grind shows as facet 63 in FIG. 13b and also effectively removes a portion of the delta point shown in dotted line in FIG. 13a. Thus a considerably wider, though overall still small portion of the whole blade profile, safe zone is provided.

Sequence of Operation—Thoracar™

The Thoracar™ emergency thoracostomy device is used to resolve a tension pneumothorax or to insert a chest tube by performing the following sequence of operations:

(FIG. 7a) Remove the bottom of the preferably sealed and sterilized case to expose the end of the trocar. The device is preferably dispensed with the twin retractable blades fully extended and ready to insert. Hold the trocar like a screw driver with the trigger button up and the handle pulled tightly against the palm. Locate the superior border of the rib most appropriate for the suspected pneumothorax or hemothorax conditions and stretch the skin up slightly with the thumb of the opposite hand (to later provide a skin flap seal over the incised wound as the tissue rearranges itself post procedure). Place the blade against the skin, parallel with the rib. Push the trocar, slowly and firmly, over the top of the rib, straight into the chest cavity. The two-part expanded blade makes a precise incision that is sized to substantially match the circumference of the self-retaining cannula and thus produces the proper amount of sharp dissection to allow gentle, easy insertion of the trocar. An abrupt drop in tissue resistance as the trocar "pops" into the chest cavity and the sound of air or sight of blood flowing through grooves in the trocar shaft indicate full penetration.

(FIG. 7b) Lift the thumb and compress the button on the side of the handle. This releases the previously spring loaded mechanism which retracts the blades to leave a relatively blunt end on the trocar. Insert the trocar then fully to the hub of the cannula.

Figure 7D:
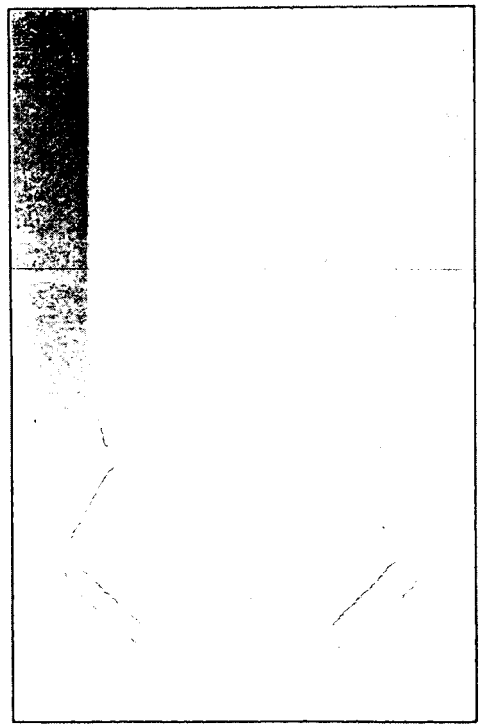
Figure 13A:
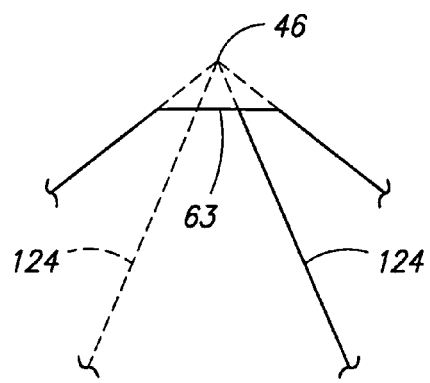
FIGS. 13a-b are partial plan details of the overlapped blade points of the blades shown in FIG. 2.

(FIGS. 7c-d) Hold the hub of the cannula against the skin with one hand and pull the trocar shaft out of the cannula with the other hand, exercising care not to twist the trocar as it is pulled (as this could prematurely dislodge the collapsible struts from their inletting in such a way as to frustrate the desirable engagement of the distal tips of the struts with the distal end of the inletting during trocar withdrawal). This action causes the network of struts on the end of the cannula, which are partially caught in semi-retentive inletting in the trocar tip (note in FIGS. 7a-b), to collapse and bend under the withdrawal force along the molded in living hinge lines and to flare outwardly, producing firm but gentle retention of the tube by its flared end of collapsed and bent network of struts within the chest cavity (FIG. 7d). Insert a standard 36 French chest tube, when necessary. Pull the delivery cannula out and over the extracorporeal excess of the chest tube. Attach chest tube to suction drainage system as appropriate.

FIGS. 17-20 show Thoracar set ready to apply. Blades 321 are open and extended as push rod 327 is locked forward. Activator spring 332 (FIG. 24) is compressed from the top as trigger block 329 hooks under trigger catch 328. Penetration detector slide 322 is pushed into shaft 323 and trigger release linkage 330 compresses activator spring 332 from the bottom. The trigger release is hooked on top of the trigger catch to set the trigger mechanism and hold detector slide 322 in an 80% retracted position. Blade reset button 327 rests in handle cap 326 recess to indicate that the blades are advanced. Collapsing struts 325 on cannula 324 are snapped into inletting on tapered dilator section of shaft 323.

Figure 21:
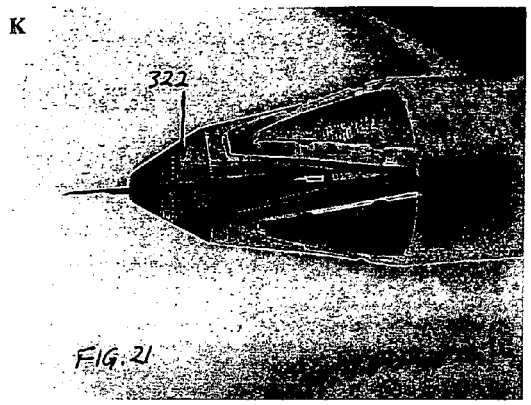
FIG. 21 is a detail perspective edge view of a blade aspect of the device shown in FIG. 14.
Figure 22:
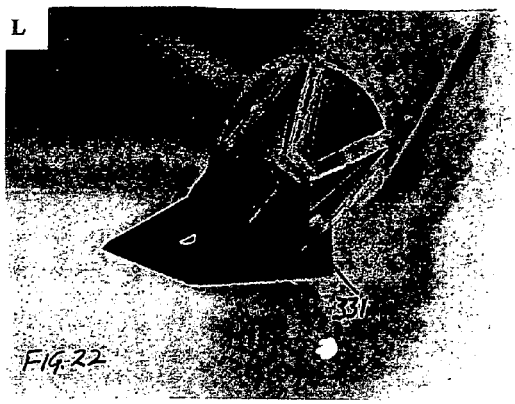
FIG. 22 is an alternate detail perspective view of a blade aspect of the device shown in FIG. 14.
Figure 23:
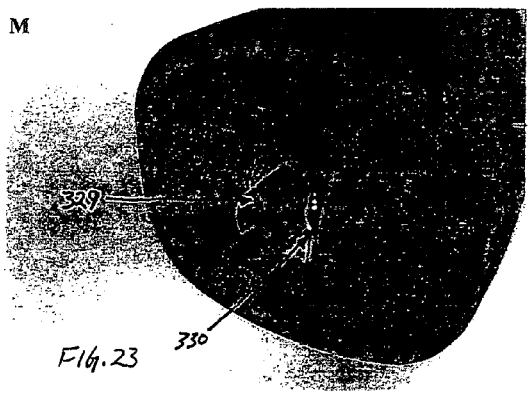
FIG. 23 is a cut away detail perspective end view of a trigger release aspect of the device shown in FIG. 14.

FIGS. 21, 22 show Thoracar as it would appear during insertion procedure. Penetration detector slide 322 is pushed back and stays rearward as the tapered tip forces open the incision made by the blades as they proceed inwards into the incision. The "speed bumps" 331 on the blunted tip slide create initial added resistance to move and hold it back. In FIG. 23, the rearward motion of the tip slide pushes trigger release linkage 330 back and unhoods the trigger release from the top of trigger catch 328 and moves it over the notch between the trigger catch and trigger block 329.

Figure 24:
FIG. 24 is an alternate cut away detail perspective end view of a trigger release aspect of the device shown in FIG. 14.
Figure 25:
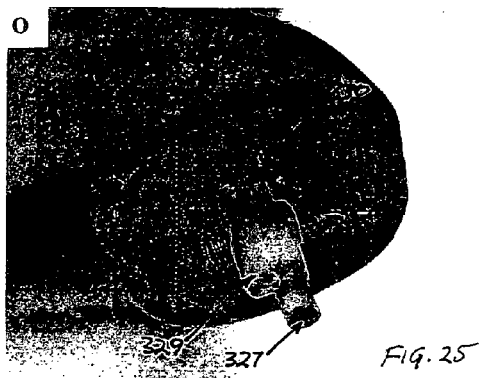
FIG. 25 is an alternate cut away detail perspective end view of a trigger release aspect of the device shown in FIG. 14.
Figure 26:
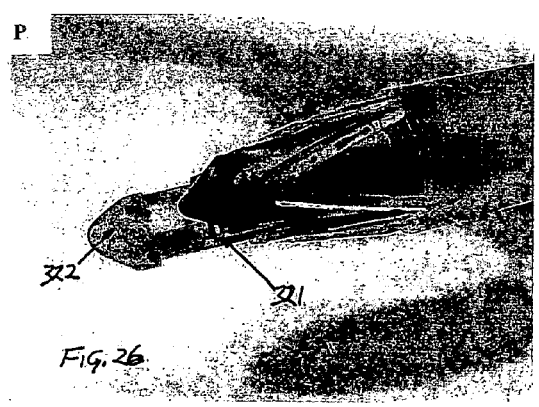
FIG. 26 is an alternate detail perspective view of a blade aspect of the device shown in FIG. 14.

FIGS. 24-26 show the release of the trigger as penetration detector slide 322 is pushed forward, at the instant of complete penetration, as the bottom of activator spring 332 retracts pull rod 327 to close and pull back blades 321 into the shaft to leave a blunt end. The reset button 327 pops out of the recess in the top of the handle cap 326 (FIG. 27) to show that the blade is retracted. Pushing the reset button back to its original position opens and resets the blades if needed.

FIGS. 28-30 show the opening of optional cannula keeper 333 to release an optional flange on cannula 324 and allow its removal from the seat in optional cannula keeper block 334. In preferred embodiments, cannula 324 is releasably engaged upon handle 323 with detents and a keyway to limit rotation of cannula 324 on handle 323 during insertion of trocar 300. In FIGS. 31, 32, pulling the shaft out of the cannula causes collapsing struts 325 to flare outward as they are lifted out of inletting in handle 323. The flared struts optionally provide light leaf-spring retention to resist displacement of the cannula. Preferably, the struts serve to effect a tissue screen for preventing clogging of cannula 324 with bits of tissue. The flare is opened easily by the insertion of a chest tube and straightens readily when the cannula is withdrawn over the installed chest tube.

Figure 14:
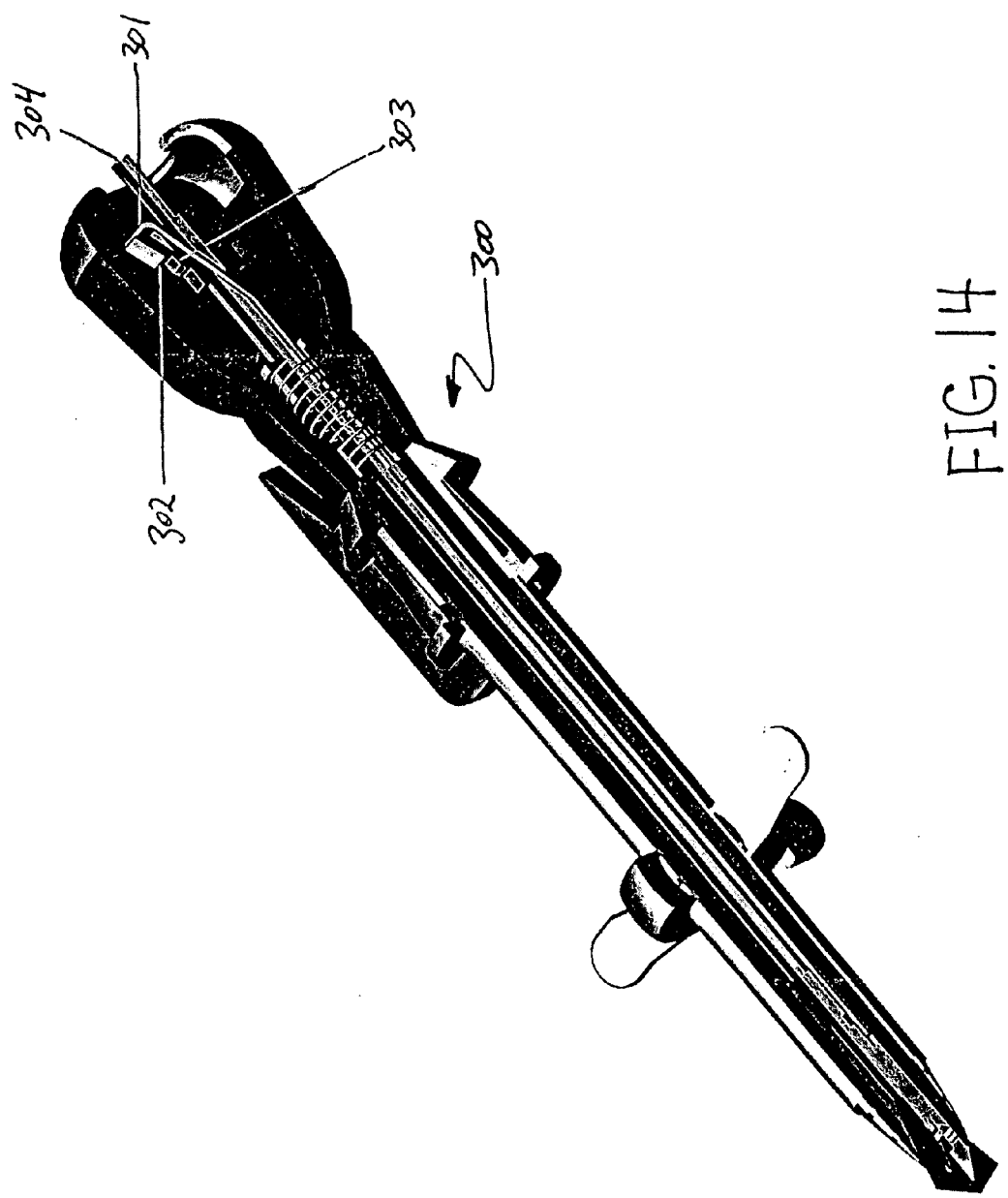
FIG. 14 is a partial perspective view of an alternate trocar device.
Figure 33:
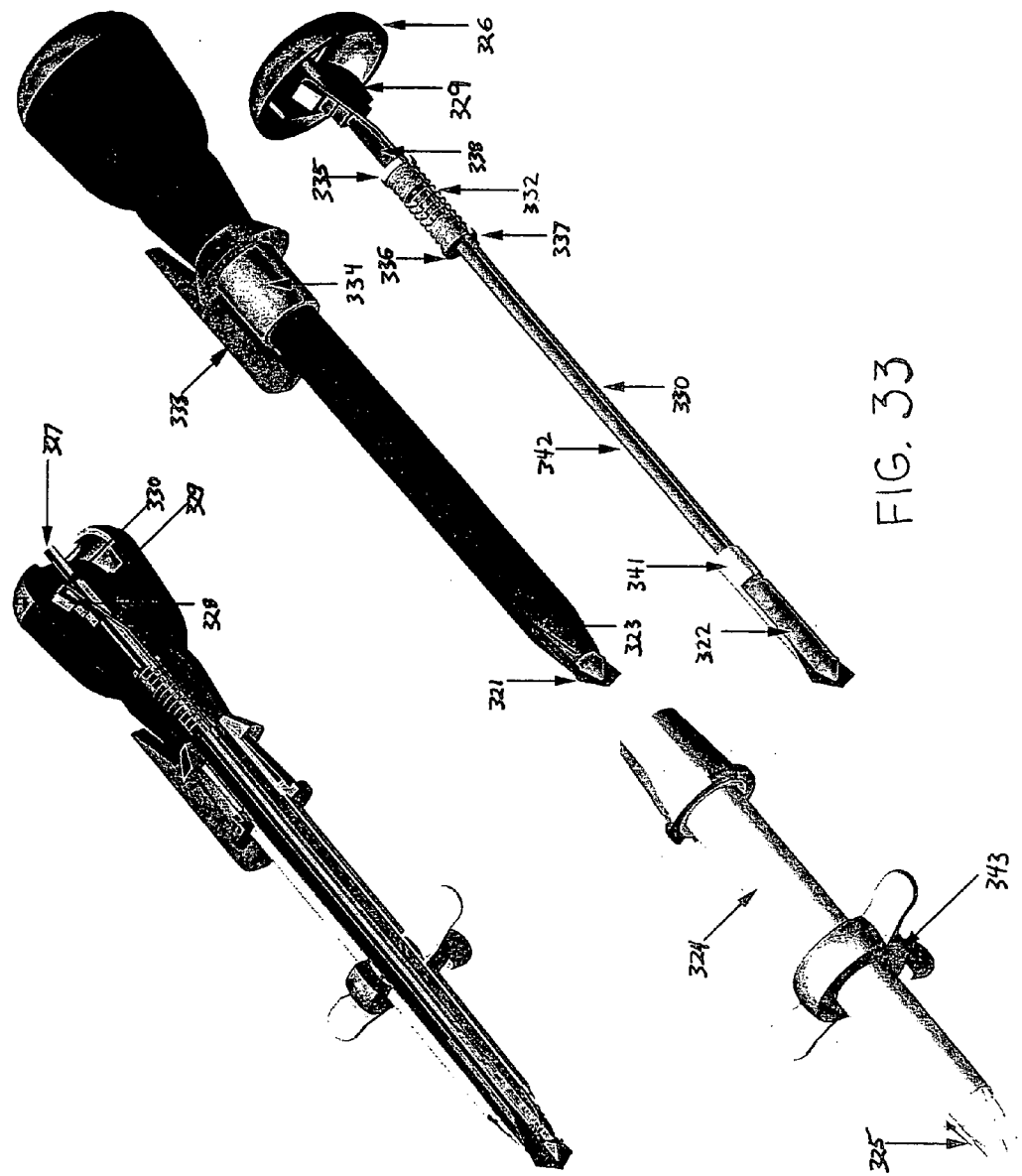
FIG. 33 is an exploded perspective view of the device shown in FIG. 14.

FIG. 33 is an exploded perspective view of the Thoracar device 300 of FIG. 14. Further details not already discussed with respect to FIGS. 17-32 are as follows. Spring stop bushing 335 is slidably engaged upon pushrod 342 and presses upon spring 332 via cylindrical bushing 338 when trigger block 329 is activated by reset button 327. Distal spring stop bushing 336 is connected directly to pushrod 342 to receive and backstop the compression of spring 332. Spring bushing 337 transmits pressure from trigger release linkage 330 to spring 332 as penetration detector 322 is driven back by insertion motion of trocar 300 through the body wall, as release trigger is effected. The camming pins for the dual trocar blades (discussed elsewhere herein) are mounted in trip block 341, which is channeled for both pushrod 342 and linkage 330 so they are free to slide within block 341. Block 341 is a snap fit into handle 323. Optional tissue stop 343 is slidably engaged on cannula 324 for optional penetration control for trocar 300.

EXAMPLES

Evaluation of Effectiveness and Safety in Acute Anesthetized Swine, Comparison with Conventional Technique Four anesthetized swine were studied acutely to evaluate prototype devices. Multiple applications of the Thoracar and standard hemostat technique (5-7 of each technique) were administered. Observations on chest access and chest tube installation were recorded. Subsequently, the animal was euthanized, the chest opened, and the interior surface of the chest was and underlying organs were examined.

Yorkshire-Hampshire crossbred swine were acquired from S&S Farms, 37441 Montezuma Valley Road, Ranchita, Calif. They were 12-18 months of age, either sex, and with body weight of 40-50 kg. A total of ten animals were used in 3 to 4-day survival experiments. All animals were survived 3-4 days and results evaluated histologically to assess the injury response. Each of the first six animals used for device performance validation received at least 3 thoracostomies and chest tube insertions using the Thoracar brand trocar, and an equal number using the conventional method (hemostat technique). The two techniques were applied to opposite sides of the chest to avoid possible confusion of results.

Surgeons' Observations Regarding the Model:

Pig skin is tougher than human skin, and more force was required to penetrate the skin with the Thoracar blades in this model than there would be in a clinical situation. The intercostal space in pigs is narrower than in humans, making the tapered trocar insertion more difficult for gaining access into the pleural cavity suing Thoracar prototypes designed with specifications for human use. The chest wall of the pig is significantly thinner than the average human with extremely little subcutaneous tissue, this creating the potential risk of deep injury with the device popping through skin and chest wall all at once in control of trocar is not absolute. Adhesions between lung and chest wall are common in pigs, increasing the chance for treating lung lesions when penetrating the chest wall with an instrument.

In summary, although the swine is a relevant model for testing this device, it probably represents a worst-case scenario in terms of mechanical difficulty and safety of gaining chest access.

Surgeons' Assessment of Physical Application of the Two Techniques:

Thoracar

Chest access with the Thoracar was performed in two stages. The first stage, cutting the skin, required a rocking motion of the device (more difficult in swine then it would be in humans). Once the skin incision was completed, axial force on the device with a slight pumping action completed penetration through the chest wall. The second stage of penetration proceeded directly after the skin incision was complete, without withdrawing the device. An adjustable mechanical stop, added as a sleeve to the outside of the device after the first animal, functioned reliably to restrict depth of penetration. Lubrication of the device was critical to reduce drag and aid in ease of penetration of the tissues. Pleural penetration led to reliable immediate retraction of the blades automatically. Penetration of the chest wall was followed by removal of the trocar shaft leaving the chest tube cannula in its place. This procedure required little effort and was almost instantaneous. Proper placement of the cannula was ergonomically and anatomically effective. Subsequent installation of the chest tube through the cannula and withdrawal of the cannula required only seconds.

Even though neither of the two surgeons had previously used the Thoracar device, the design and handling properties were logical and intuitive, and the learning curve for assimilating the technique for safe and efficient chest tube placement was very short, requiring minimal experience to achieve competency with the technique. This ease in assimilation should extrapolate to physicians in general and produce a more consistent, standardized approach to chest tube placement and decreased risk for error and patient injury.

Conventional Hemostat Technique

Chest access with the standard hemostat technique was a three-step procedure. The first step was a simple incision of the skin with a scalpel. The second step was blunt dissection with a hemostat to create a hole through the intercostal space. The hemostat was then withdrawn from the wound channel. Adequacy of the size of the hole depended on intuition, feel and experience, and could not be verified except by trial and error. Installation of the chest tube involved a third step, in which the proximal end of the tube was inserted into the previously created hole in the intercostal space and pushed through the hole into the pleural space. Because the skin incision is offset from the intercostal hole (standard procedure), and because the hole is obscured by blood from the blunt dissection, insertion of the tube was performed by feel without visual aid. When the intercostal hole size was not adequate, repeat blunt dissection with the hemostat was required. Without ability to visually locate the first hole, sometimes a second hole was created, inadvertently.

Surgeons' Assessment of Results of the Two Techniques:

Thoracar

The Thoracar procedure was judged to be safe, simple and consistent. The skin incision was uniform. In initial trials with the 13 mm blade design, the skin incision was oversized, but with the 9 mm blades the skin incision was a snug fit for the chest tube. Variation in incision length was only ±1 mm. Chest access was quick and reliable without excessive bleeding. Blade retraction was associated with an audible "click" and occurred automatically on entry into the pleural space. Over-penetration into the chest cavity (before installation of the adjustable mechanical stop) did not result in significant lung lesions, indicating that the profile of the trocar with blades retracted was non-traumatic. Chest tube insertion was simple, and correct fit was certain. Occasional superficial lung lesions were observed. There was occasional observation of blood in the tube, which was believed to come form the chest was dissection and did not persist or become significant in any animal. Each animal had placement of chest tubes while on positive pressure ventilation with inspiratory hold during placement, in order to mimic more closely the clinical setting and maximize the potential for pulmonary injury. Despite these worst-case conditions, there was no evidence of excessive lung penetration, and blade penetration occurred as designed on entry even though the lung was held expanded against the chest wall.

Conventional Hemostat Technique

The standard hemostat technique was judged to be safe, but involved more steps, was less consistent, and took more time. The skin incision was more variable, and the incision invariably exceeded the minimum size necessary for the chest tube. Results of blunt dissection through the intercostal space with the hemostat were variable and sometimes resulted in noticeable bleeding. Chest tube insertion required an inconsistent insertion step, and the result was associated with some uncertainty due to variability in size of the intercostal lesion and difficulty location the hole. There was frequent evidence of superficial lung lesions when placed under positive pressure ventilation and a small amount of blood in the chest tube.

Summary of Results from Pilot Animal Testing:

Results from pilot tests indicated the Thoracar was superior to the hemostat technique in that it required fewer steps, took less time, was more uniform in its application, and its results were more consistent. There was also a suggestion for greater safety, presumably associated with the procedure being more uniform. The Thoracar procedure was safe, even with positive pressure ventilation and inspiratory hold during placement, indicating that the Thoracar design, even with its sharp blades, effectively protects the thoracic organs from lacerations and bleeding. The technical challenge of Thoracar insertion is significantly less that the standard hemostat technique and should produce increased consistency among practitioners and minimize patient morbidity. These test were successful in providing data to guide design development and in verifying acute in vivo device performance.

Test Safety and Effectiveness in a Survival Surgery Swine Model

The Thoracar design resulting form interactive testing in acute pilot experiments was evaluated in two pigs allowed to recover from surgery. The hemostat technique was also used for comparison. The surgeons and the study pathologist advised that the short-term injury response would be more likely to show differences between techniques than the longer-term healing response. Accordingly, the postoperative survival period was shortened to four days from three weeks as originally proposed. The number of chest tube insertions was limited to three of each technique in each animal, and the two techniques were applied to opposite sides of the chest. The acute studies indicated too many holes and same-side application of the two techniques crated the potential for confusion when comparing internal and external lesions. This was largely due to the fact that the skin incision is offset from the intercostal incision.

Observations at Surgery:

Thoracar

Chest tubes were successfully installed in all 6 sties attempted with the Thoracar. As the cannula passed through the chest wall and into the pleural space, an audible "click" was heard, signaling retraction of the blades. In 2 cases the mechanical stop was inadvertently left off the trocar, and penetration proceeded an estimated 3-5 cm further into the plural cavity than was necessary, due to the thinness of the chest wall and unpredictable release of resistance as the trocar passed through the chest wall. Even with the deeper penetration without the stop, no significant blood was observed in the chest tube, nor was there any air issuing from the tube (the animals were on positive pressure mechanical ventilation), suggesting an absence of significant lung lesions.

In 4 of 6 cases with the Thoracar, the chest tube cannula was installed in a single step and the chest tube was placed through the cannula immediately thereafter. With single-step Thoracar insertion, the total time from skin incision to tube placement averaged 21 seconds. In 2 cases, 2 attempts were needed to successfully insert the trocar through the intercostal space after the skin incision was made, effectively doubling the installation time. The problem encountered was due to difficulty negotiating the pig's narrow intercostal space with the trocar. Overall, the total time from incision to chest tube installation, including the 2 cases with 2 attempts, was 29.5±6.5 seconds (average ±SEM). The range was 16 to 50 seconds.

Conventional Hemostat Technique

Chest tubes were successfully installed in all 6 sties attempted with the hemostat technique. After the skin incision was made, a curved hemostat was used to create a hole between the ribs. Entry into the pleural space was associated with a sudden reduction in resistance while pushing the hemostat. The jaws of the hemostat were then expanded to enlarge the hole to accept the chest tube. The hemostat was withdrawn and chest tube inserted into the hole just created. Sometimes the end of the tube was clamped with the hemostat and the hemostat used to guide the tube into the hole. Occasionally, bleeding resulted from the blunt dissection. Blood was present in the chest tube after installation, but no air leakage was detected. Presumably the blood was primarily from the blunt dissection in the chest wall.

In 4 of 6 cases with the hemostat technique, the chest tube was installed in the standard three steps (skin incision, creation of hole between the ribs with a hemostat, and chest tube insertion). When no problems were encountered, the total time from skin incision to tube placement averaged 42 seconds. In 2 cases, 2 or 3 attempts were needed to crate a hole between the ribs through which the chest tube could be placed. The problem was primarily due to difficulty in relocating the hole after the hemostat had been removed, and secondarily due to the hole being too small, which required repeating blunt dissection with the hemostat. In one case a second hole was inadvertently created while trying to relocate and widen the hole. This was only discovered at autopsy and was not apparent at the time of surgery. Overall the total time from incision to chest tube installation, including those procedures with multiple insertion attempts, was 55.5±11.0 (average ±SEM). The range was 39-88 seconds.

Observations at Necropsy:

Thoracar

Skin incisions were unremarkable, with edges accurately apposed and sutures in place. There was no swelling or redness of the skin. The lesions on the inner surface of the chest wall were beginning to heal, with no or minor swelling. One minor superficial lung lesion was observed in one of the two animals.

Conventional Hemostat Technique

Skin incisions had edges accurately opposed and sutures in place, but there was minor to moderate swelling and redness of the skin. The lesions on the inner surface of the chest wall were beginning to heal with minor to moderate swelling. One minor superficial lung lesion was observed in one of the two animals.

Pathologist's Observations from Histology:

Histological comparison of the hemostat method and the Thoracar method reveals a similar degree of trauma and inflammatory response. However, the Thoracar tract through the chest wall is filled with serum, fibrin and small amounts of clotted blood, while the traditional chest tube trace is filled with only clotted blood. This is a minor difference, but the fibrin and serum debris will be absorber more rapidly and with less histiocytic infiltration than the blood clot, which may be less irritating to the patient and lead to less ultimate scar formation.

Other Examples

Figure 15A:
FIGS. 15a-d are photographs of the device shown in FIG. 7, in test sequence of operation.
Figure 15B:
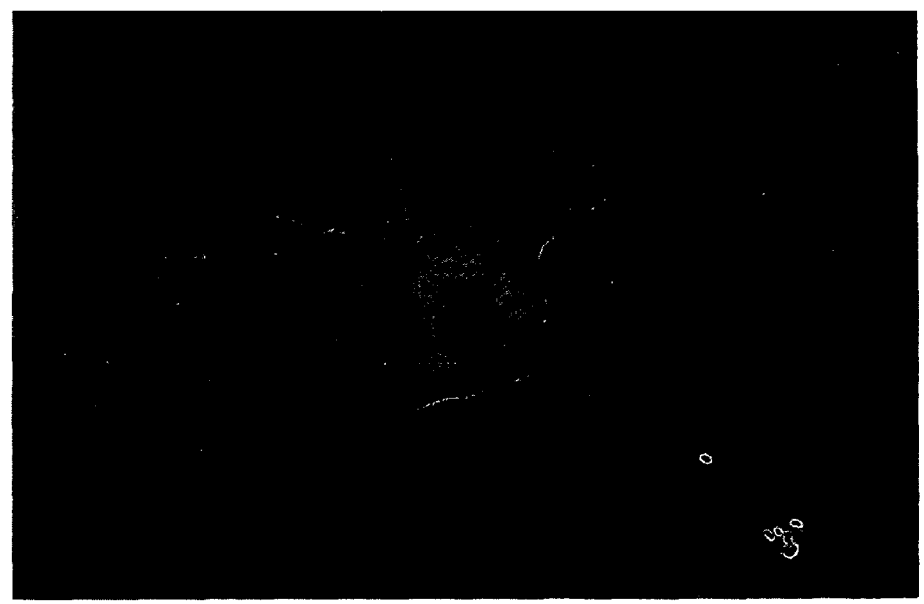
Figure 15C:
Figure 15D:
Figure 16B:
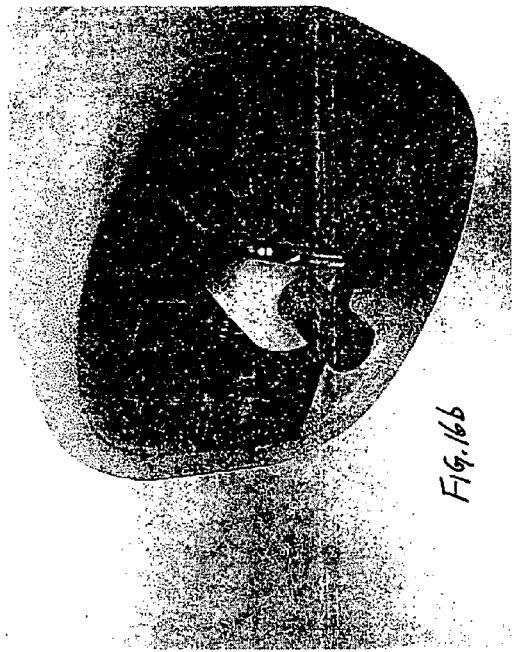
FIGS. 16a-d are partial perspective detail views of the trigger end of the device shown in FIG. 14.
Figure 16D:
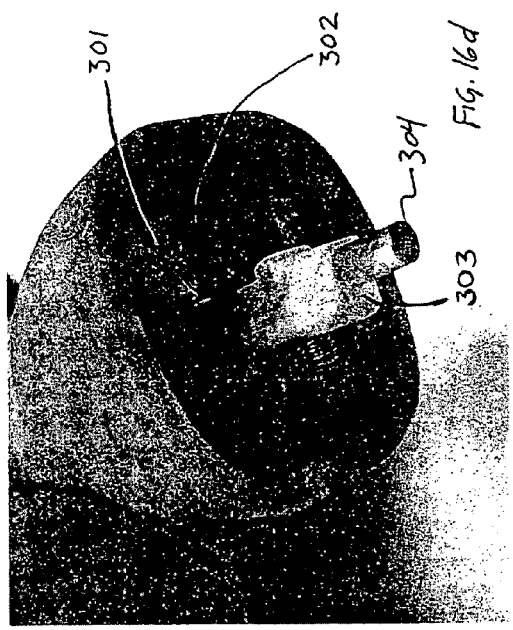
Figure 16A:
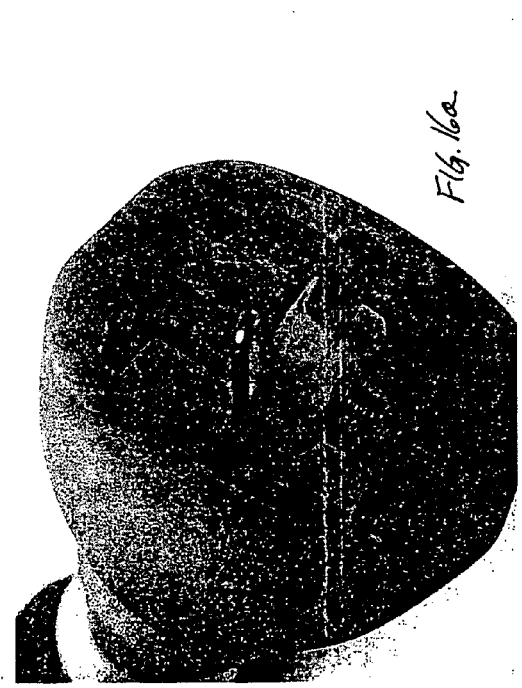
Figure 16C:
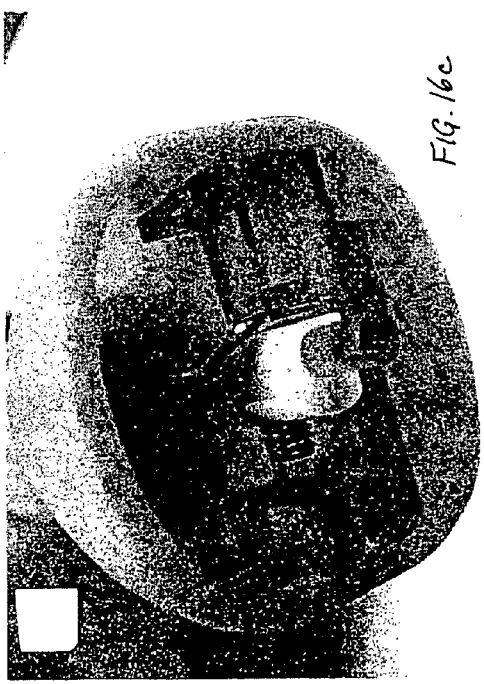
Figure 17:
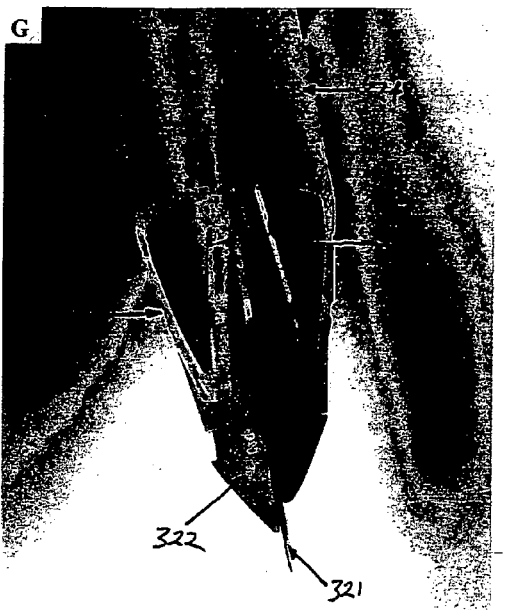
FIG. 17 is a detail perspective edge view of a blade aspect of the device shown in FIG. 14.
Figure 19:
FIG. 19 is a detail perspective side view of a blade aspect of the device shown in FIG. 14.
Figure 18:
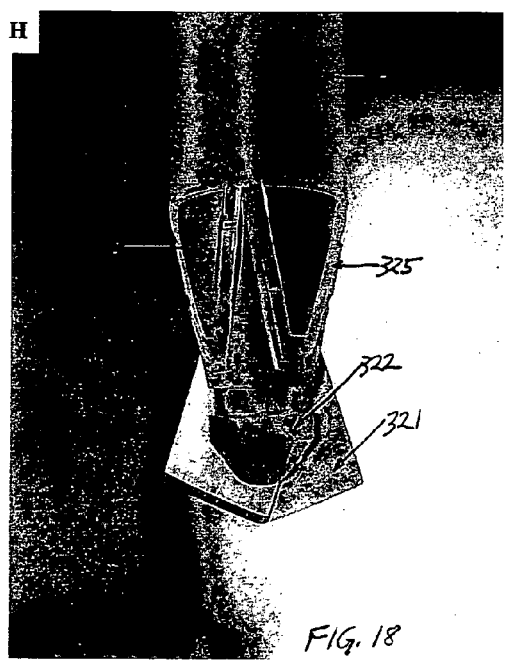
FIG. 18 is a detail perspective end view of a reset button aspect of the device shown in FIG. 14.
Figure 20:
FIG. 20 is a cut away detail perspective end view of a trigger release aspect of the device shown in FIG. 14.

A prototype thoracostomy trocar and chest tube delivery system has been tested on a sheep cadaver immediately post mortem, in accordance with acceptable animal testing protocols (see FIGS. 15a-d). Three different operators were able to easily and precisely insert it and deploy its delivery cannula. FIG. 15a shows grip of device shown in FIG. 7 in the hand of an operator, preparatory to insertion; FIG. 15b shows the device inserted almost fully, and the cannula partially inserted (note tight fit of tissue to cannula); FIG. 15c shows the trocar portion of the device now removed, and the cannula fully inserted and self retained. Upon post procedure dissection (FIG. 15d), no evidence of damage to the lung was noted, even though it was hyper-inflated during the puncture. In addition, no damage to the superior border of the rib was noted. In fact, a concerted effort was made to actually penetrate the hyper-inflated lung directly after the chest was opened, and was not possible despite multiple 10 cm+ straight thrusts of the trocar.

These encouraging results were obtained with a trocar that had a straight 9 mm shaft, two 9 mm blades and delivered a 10 mm O.D. cannula. As it has been recommended that a 36 size French chest tube is the minimum acceptable size for comprehensive management of a severely injured chest where protracted bleeding may occur, the preferred delivery cannula is therefore slightly larger than 13 mm I.D., to accommodate the 13 mm O.D. 36 French tube.

Laparoscopic Embodiments and Preferred Trocar Double Set Triggering

The following descriptions refer to an embodiment of trocar 300 (FIGS. 14 & 16) that is used to penetrate the abdominal wall to install a laparoscopy port. As with other embodiments no scalpel incision of the dermis is required to start the application process. The V-shaped, twin-bladed incision mechanism built into the trocar tip makes a precise incision that is matched to the circumference of the trocar cannula as it is slowly pushed straight through the abdominal wall with very little tenting. This produces an incision of exactly the right length every time.

As the tip proceeds through the dermis, the spring-loaded, blunt wedge shaped penetration detector slide on one side of the conical trocar tip is pushed back slightly as the tapered shaft meets resistance from the abdominal wall tissue, and the trocar wedges or dilates the incision without further cutting. This resistance releases the trigger that allows the spring to push the blunt wedge forward. Once the resistance of the dermal layer is passed, and the tip enters the soft subcutaneous fat layer, the wedge can slide with relative freedom ahead of the blades, and in so doing activates the retraction linkage which automatically snaps the blades closed and pulls them back into the shaft.

When the tip slide linkage is extended and the blades are in the retracted position, trigger block 303 (FIG. 16*d*) rests against the side of the trigger catch 302. The top of trigger release linkage 301 is now under trigger catch 302 and rests against the side of trigger block 303. A groove formed into the bottom of trigger catch 302 (location also indicated at 302, FIG. 14), similar to the groove in the top of the catch which holds the trigger release as in FIG. 16*a*, captures the top of linkage 301 and keeps it from moving up if the tip slide is compressed. This locks the blunt, hemi-conical slide locks into the extended position which instantly transforms the cutting trocar into an asymmetrical blunt conical configuration before the tip fully penetrates the abdominal wall.

When penetrating the body wall after an initial incision, a preferred blunt tip seeks the path of least resistance, dissecting between the abdominal muscle and fascia fibers as well as the peritoneum. The subdermal layers are thus penetrated by separation and not by transection as the asymmetrical wedge is pressed between the fibers into the abdominal cavity. The resulting slit-like opening is the smallest possible fits the ports tightly to prevent displacement and will naturally reapproximate after the port is removed. This helps avoid the formation of a ventral hernia after surgery.

The use of the disclosed laparoscopic trocar greatly reduces the possibility of medical error associated with the placement of laparoscopic ports by assuring that an ideally dimensioned skin incision and abdominal wall puncture is safely and simply made in a single stroke.

The single-patient-use trocar can be reset and used to install all of the large ports needed for each case. It has been designed with low-cost mass production in mind, has fewer parts and a less complicated mechanism than currently available cutting trocars, and is believed to cost less to make.

Thoracostomy Trocar Reactivation

When necessary to reactivate the blade mechanism during the application, wider 'sear' portion of the thoracostomy version of the trocar comes into play. The end of the blade retraction linkage 304 (FIG. 14) is pushed in through the hole in the end of the handle. The sear on the side of trigger block 3030 (FIG. 14) is hooked under the trigger catch 302 as in FIG. 16a and FIG. 14. When the blade linkage is cocked and the blades are extended, the side of trigger block 303 which is wider below the sear pushes the trigger release linkage out from under the trigger catch. If the extended slide is compressed in this bladed-cocked position the trigger release linkage can slide up, around and over the top of the catch (as in FIG. 16b) and into a position which will allow the release to move down between the catch and the block (FIG. 16c), and set off the retraction linkage upon full penetration of the body wall.

Spring metered pressure on the penetration detection allows the device to perform the same each time no matter who is operating it. Varying the speed and initial penetration force slightly does not change the action of the spring. When sufficient axial pressure has been exerted, the detector is initially pushed back under spring pressure from its starting position slightly beyond the tip of the extended blade as the blunt, curved end of the tapered wedge shaped detector is engaged by the skin.

As the trocar is advanced, the detector comes to rest alongside the tapered wedge shape tissue deflecting/dilating surface on the opposite side of the trocar tip to form the incision/wound dilator. As the detector moves back, the stationary blade's point emerges. The skin has been stretched a metered amount by the blunt detector, making it easy for the double-beveled point to start penetration the tightly drawn tissue. As the angles, left and right single-beveled slicing portions of the blade slide through, the width of the skin incision and resulting wound channel are defined by the sharp corners on the left and right trailing edges of the open and extended blade unit. All operators will produce an optimally sized incision. This eliminates the risk of making an improperly dimensioned incision when cutting free hand with a scalpel as a separate step from trocar insertion.

The width of the detector is narrower than the width of the extended blades, so it can start to move forward alongside the blade tip into the body cavity, once penetration has been achieved, before the trailing edges make it through the channel, thus causing the blade to close and retract before a full-width incision is made into the peritoneum. In the laparoscopic version, this allows the highly compliant peritoneum to be stretched tightly around the trocar cannula by the tapered end of the shaft, thus assuring a gas tight seal around the tube. At the same time, the end of the shaft is made blunt and no cutting points or edges are exposed. This eliminates the possibility of laceration or penetration of deep structures. All of these functions are accomplished automatically as the operator simply pushes the trocar through the skin into the body cavity. This tool, with its built-in safety feature makes it much simpler and safer to apply a trocar and delivery cannula, as compared to Sauer's. Precise skin incision, gentle wound dilation, automatic retraction of the blades at the instant of penetration, and installation the cannula are accomplished in a single stroke.

The disclosed device has a spring activated penetration detector which exerts a metered amount of blunt dissecting force along side the blade as it advances through the tissue, irrespectively of the force being applied to the trocar. As the point begins to penetrate into the body cavity, the beveled end of the detector can slide in along side the blade and thus releases a linkage which automatically closes and retracts the blades. A single spring operates both the penetration detector and the blade retractor.

The blades can be made to retract at any time by pulling back slightly on the trocar. This allows the spring motivated detector to slide forward, relative to the rest of the trocar, and set off the retractor. This allows the surgeon to then blunt dissect the rest of the way into the body cavity if he so chooses. The blades can be easily reopened and advanced, if need be, without fully withdrawing the trocar from the wound channel by the push of a button on the end of the trocar handle. The mechanism then functions again just as before.

Fabrication Notes

One method for making the preferred thin walled, single-use, collapsing polypropylene cannula part is injection molding. Blades are preferably stamped from stainless steel sheet stock, and then sharpened and polished in a precision grinding machine. What is desirable is maximum 'scalpel' sharpness for the given blade material (believed to be about 17.5 degrees of edge angle for stainless steel), so that the double thick, double beveled overlapping blade points will be 'half scalpel sharp'. Sharper than a scalpel is generally not preferred due to increase accidental cutting danger, but would not depart from the scope of the invention; less sharp blades may be made to serve but will present increase penetration resistance with attendant danger of accidental overpenetration as the body wall is penetrated. With that in mind a range of blade edge angles of 17° to 19° are preferred, with 17° more especially preferred.

The handle and shaft portion of the disclosed devices are also preferably injection molded, and have a two piece hermaphrodite part design that allows identical halves to be assembled face to face with the moving parts (retractor shaft, stainless steel cross pins, trigger pin, spring & washer) sandwiched between them. In addition, the blades are also hermaphrodite parts, for mounting face to face. This greatly reduces tooling and production costs of the preferably disposable devices, while increasing uniformity and integrity.

Preferred mating of the variously disclosed half parts is by electronic or ultrasonic welding, or glue, and especially preferred are hermaphrodite molded pin-and-cup structures or the like. These molded structures in the half parts will, when the preferably identical part halves are turned to face each, be appropriately reciprocally placed, as will be appreciated by those skilled in the art, for mating and secure joinder.

Disclosed devices have so far been injection molded under ISO 9001 industrial standards at Mold Rite, Inc., Maltby, Wash. The handle and shaft are preferably made of polycorbonate and the cannula out of polypropylene. A hardened die is made and the blades are punched from stainless steal sheet stock. The stampings are ground and polished on a machining set-up that is built for that purpose, the workings of which will be familiar to those skilled in the metal working arts. The components (illustrated in exploded schematic FIG. 33) are assembled and packaged under clean room conditions and commercially gamma ray sterilized. The design and function of the device shown in FIGS. 14, 16 and 17-32 are the same as the single slide design used in the survival swine tests.

With regard to systems and components above referred to, but not otherwise specified or described in detail herein, the workings and specifications of such systems and components and the manner in which they may be made or assembled or used, both cooperatively with each other and with the other elements of the invention described herein to effect the purposes herein disclosed, are all believed to be well within the knowledge of those skilled in the art. No concerted attempt to repeat here what is generally known to the artisan has therefore been made.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications within the legitimate and valid scope of the appended claims, appropriately interpreted in accordance with the doctrine of equivalents.

I claim:

1. A surgical cutting tool comprising an automatically retractable blade assembly having a cam action double blade and a blunt penetration detector slide and a blade lock, which are operably interengaged as a double set of auto blade retraction releases, whereby triggering of the blunt penetration detector slide release frees the blade lock that holds back a second release, which when freed in turn, causes a set of blades to immediately retract to within a sheath.

2. A surgical cutting tool comprising an automatically retractable blade assembly having a cam action double blade and two sequentially operating auto blade retraction releases, a first blunt penetration detector slide release adapted to be activated by insertion of the tool into a body wall, to thus push back the first blunt release against spring tension into position to free a blade lock, such that when the tool penetrates through the body wall into a body cavity the blunt penetration detector slide is urged into forward motion by the spring, causing the retractable blade assembly to immediately retract to within a sheath.

3. A surgical cutting tool comprising an automatically retractable blade assembly having a cam action double blade and a two-stage auto blade retracting release mechanism, a first stage blunt penetration detector slide release adapted to be pushed back by insertion of the tool into a body wall, to thus move the blunt first release into position to free a blade lock, thereby activating a second stage release which, upon penetration of the tool through the body wall into a body cavity and forward motion of the blunt penetration detector slide, causes the retractable blade assembly to immediately retract to within a sheath.

* * * * *